(12) United States Patent
Kuracina et al.

(10) Patent No.: US 8,100,857 B2
(45) Date of Patent: Jan. 24, 2012

(54) METHOD AND APPARATUS FOR INDICATING OR COVERING A PERCUTANEOUS PUNCTURE SITE

(75) Inventors: Thomas C. Kuracina, Ojai, CA (US); Randall E. Ohnemus, Ventura, CA (US); Richard Cohen, Ventura, CA (US); Wilfrid E. Des Laurier, Reedley, CA (US)

(73) Assignee: B. Braun Melsungen AG, Melsungen (DE)

( * ) Notice: Subject to any disclaimer, the term of this patent is extended or adjusted under 35 U.S.C. 154(b) by 487 days.

(21) Appl. No.: 11/476,507

(22) Filed: Jun. 27, 2006

(65) Prior Publication Data

US 2007/0027429 A1   Feb. 1, 2007

(51) Int. Cl.
*A61M 5/00* (2006.01)
*A61M 5/32* (2006.01)

(52) U.S. Cl. ............ 604/110; 604/198; 604/272

(58) Field of Classification Search ............ 604/52, 604/110, 116, 180, 192, 198, 263, 272
See application file for complete search history.

(56) References Cited

U.S. PATENT DOCUMENTS

| | | | | |
|---|---|---|---|---|
| 2,627,269 | A * | 2/1953 | McGregor | 604/2 |
| 4,243,035 | A * | 1/1981 | Barrett | 604/1 |
| 4,755,170 | A * | 7/1988 | Golden | 604/513 |
| 4,955,866 | A * | 9/1990 | Corey | 604/192 |
| 5,120,321 | A * | 6/1992 | Oksman et al. | 604/198 |
| 5,423,766 | A * | 6/1995 | Di Cesare | 604/192 |
| 6,524,284 | B1 * | 2/2003 | Marshall | 604/272 |
| 6,749,588 | B1 * | 6/2004 | Howell et al. | 604/164.08 |
| 6,967,261 | B1 * | 11/2005 | Soerens et al. | 602/48 |
| RE38,996 | E * | 2/2006 | Crawford et al. | 604/263 |
| 7,066,908 | B2 * | 6/2006 | Kuracina et al. | 604/116 |
| 2007/0093760 | A1 * | 4/2007 | Wexler | 604/187 |

* cited by examiner

*Primary Examiner* — Kevin C Sirmon
*Assistant Examiner* — William Carpenter
(74) *Attorney, Agent, or Firm* — Tim L. Kitchen; Richard J. Apley

(57) ABSTRACT

Systems and methods are disclosed for identifying and deploying a protective cover about a percutaneous puncture site formed by a hypodermic needle. In the preferred embodiment, a marking agent or puncture site covering, the latter of which preferably takes the form of a bandage, is releasably secured upon either the needle hub of the hypodermic needle or on a sliding member or sleeve axially moveable along the length of said needle that forms a marking or detaches therefrom once compressed about the puncture site.

11 Claims, 26 Drawing Sheets

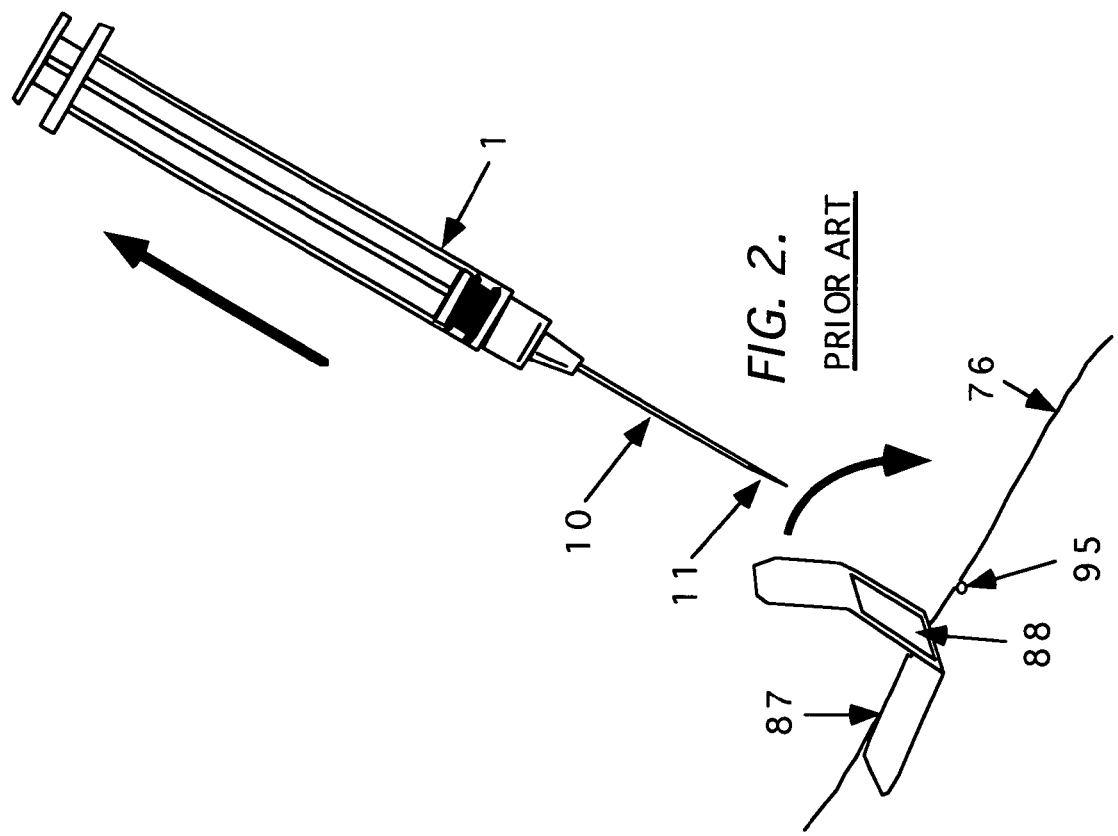
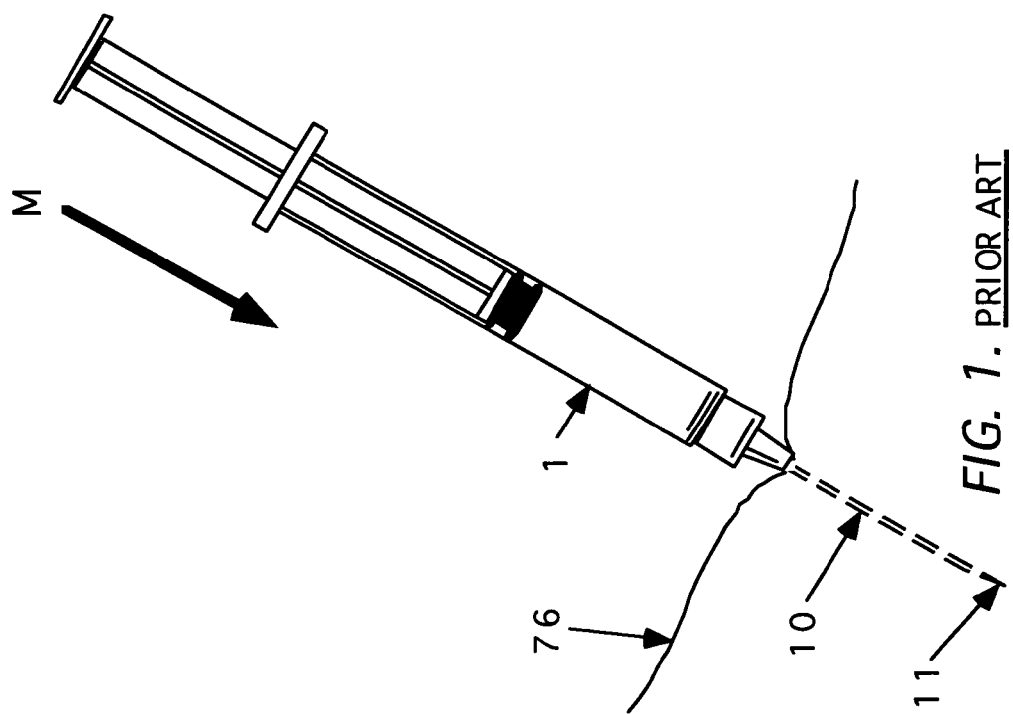

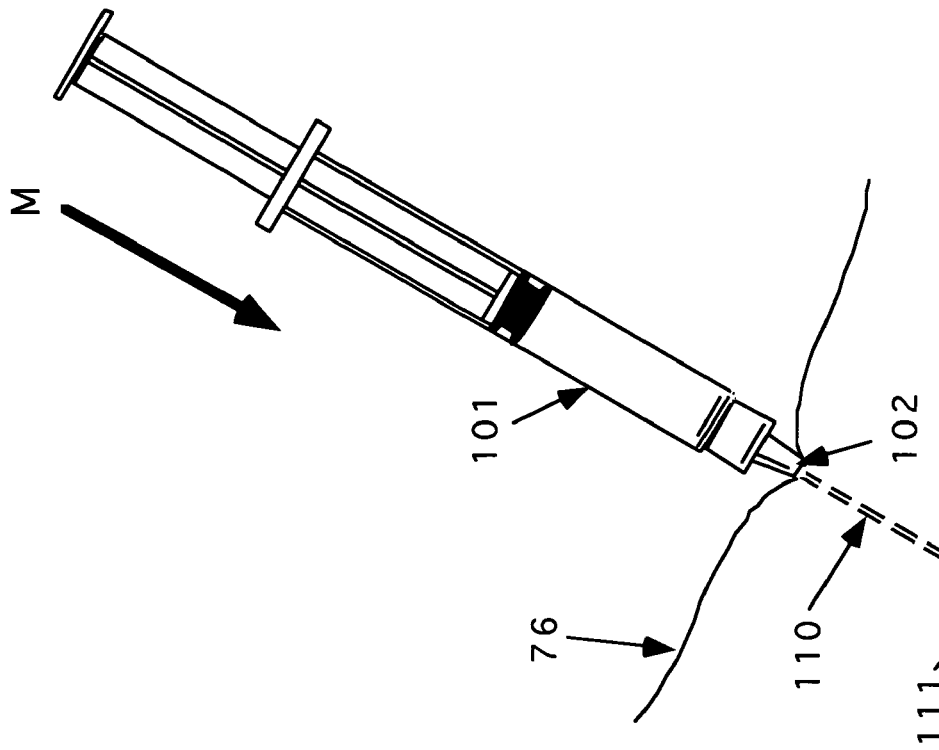
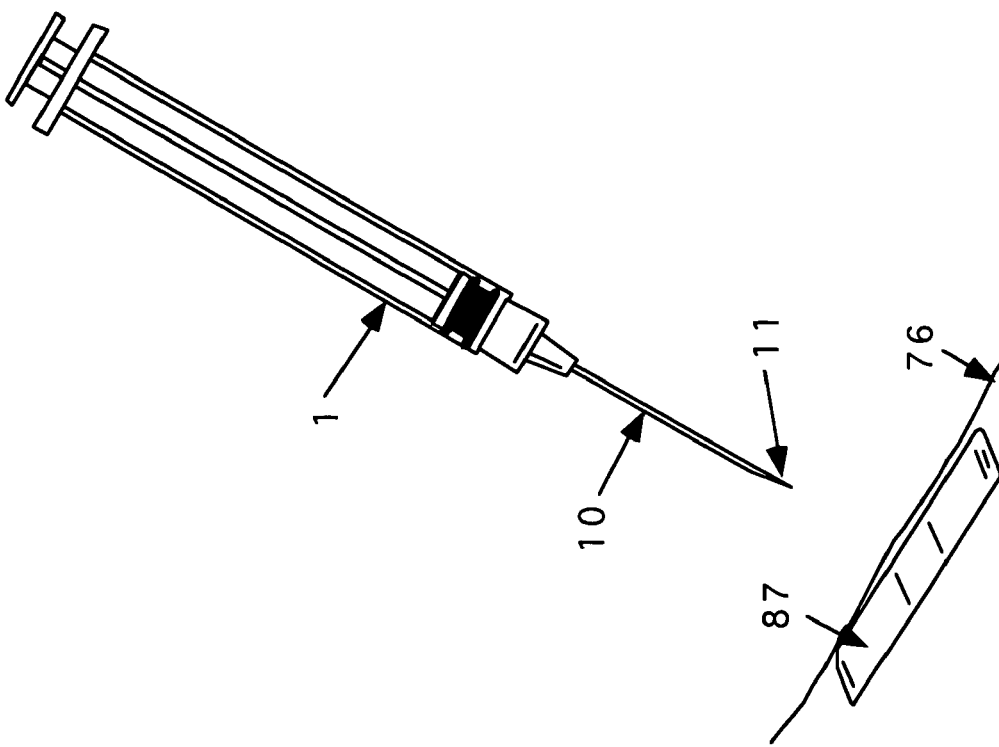
*FIG. 3.* PRIOR ART
*FIG. 4.*

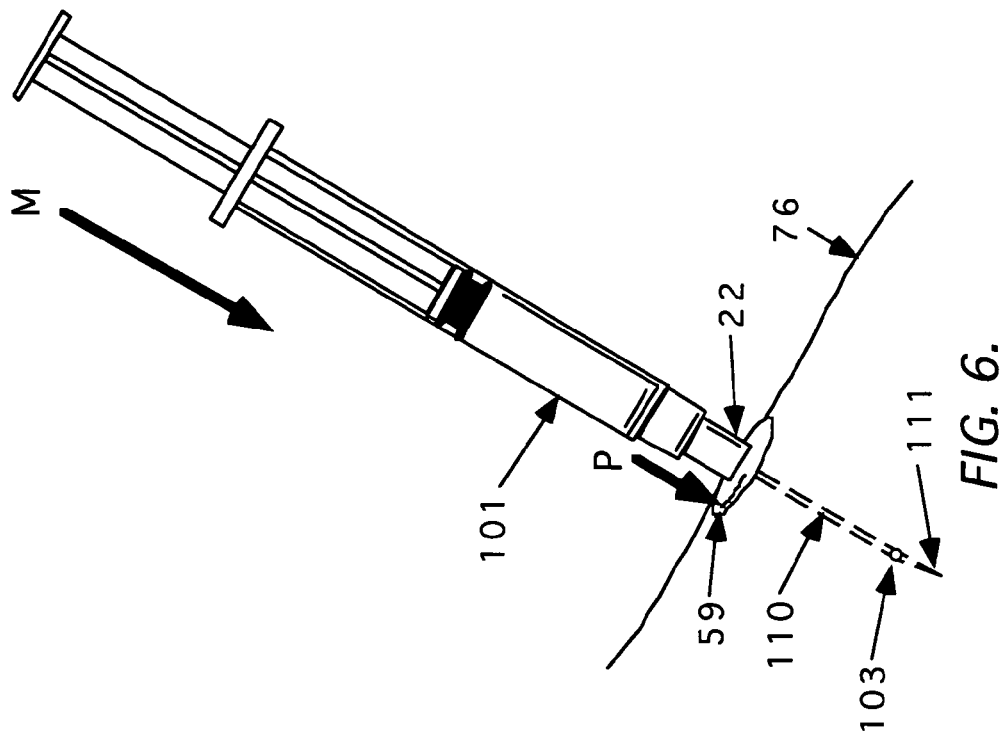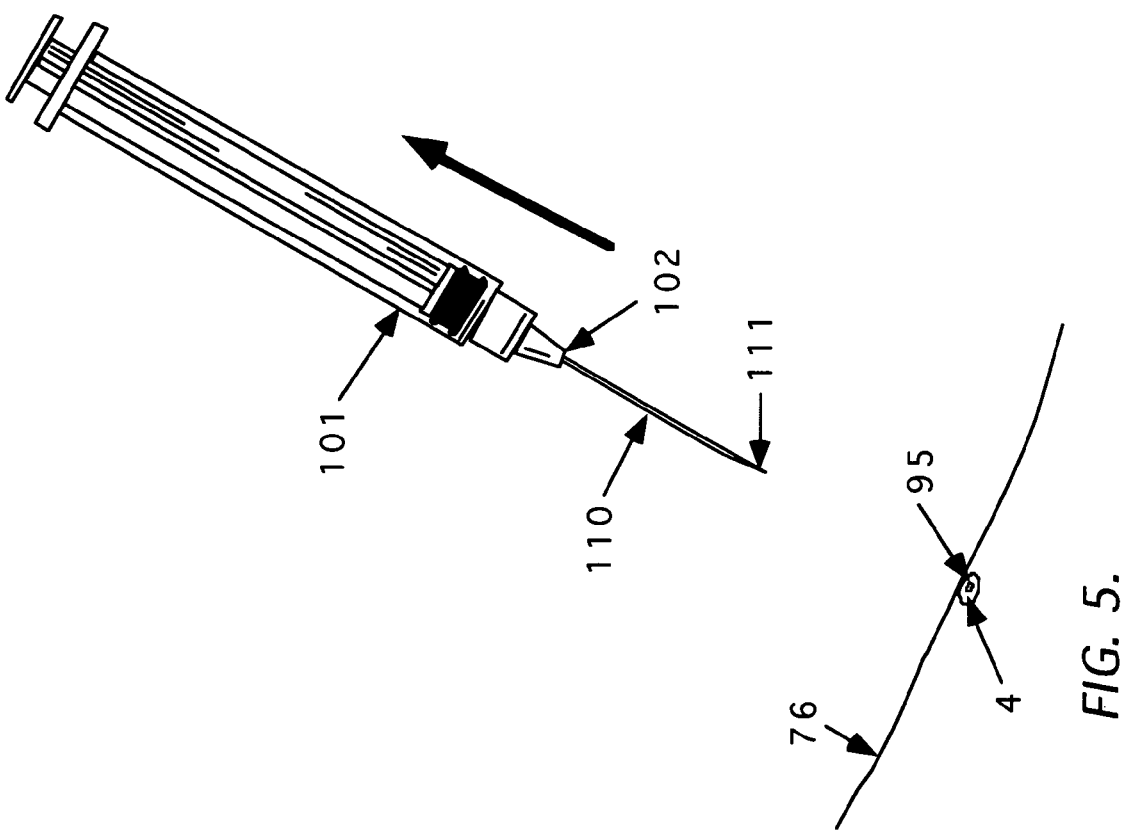

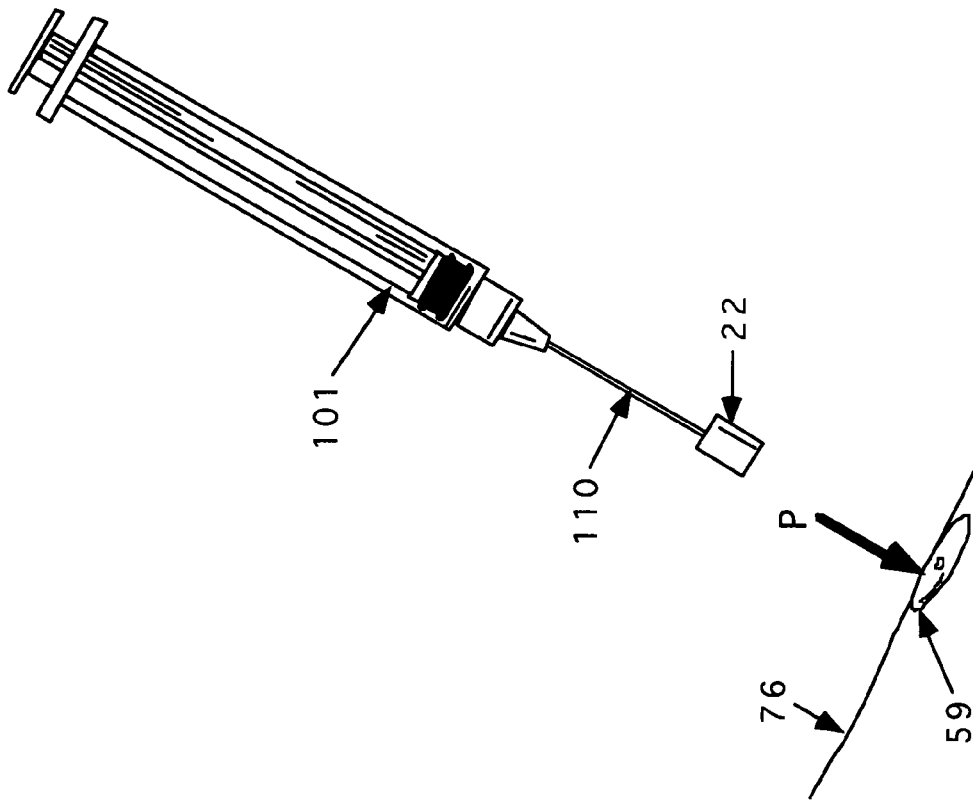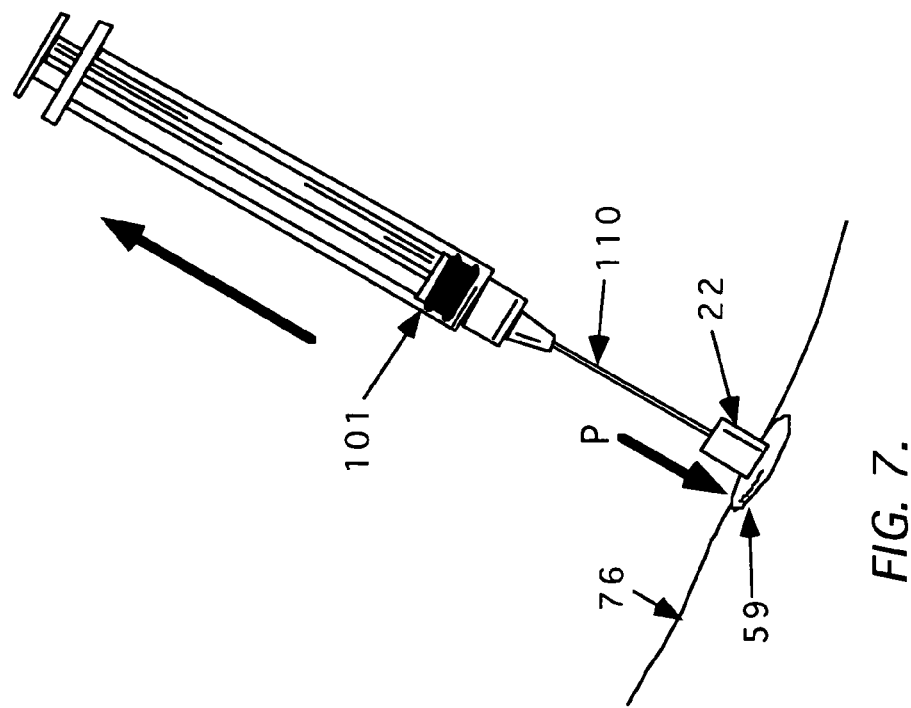

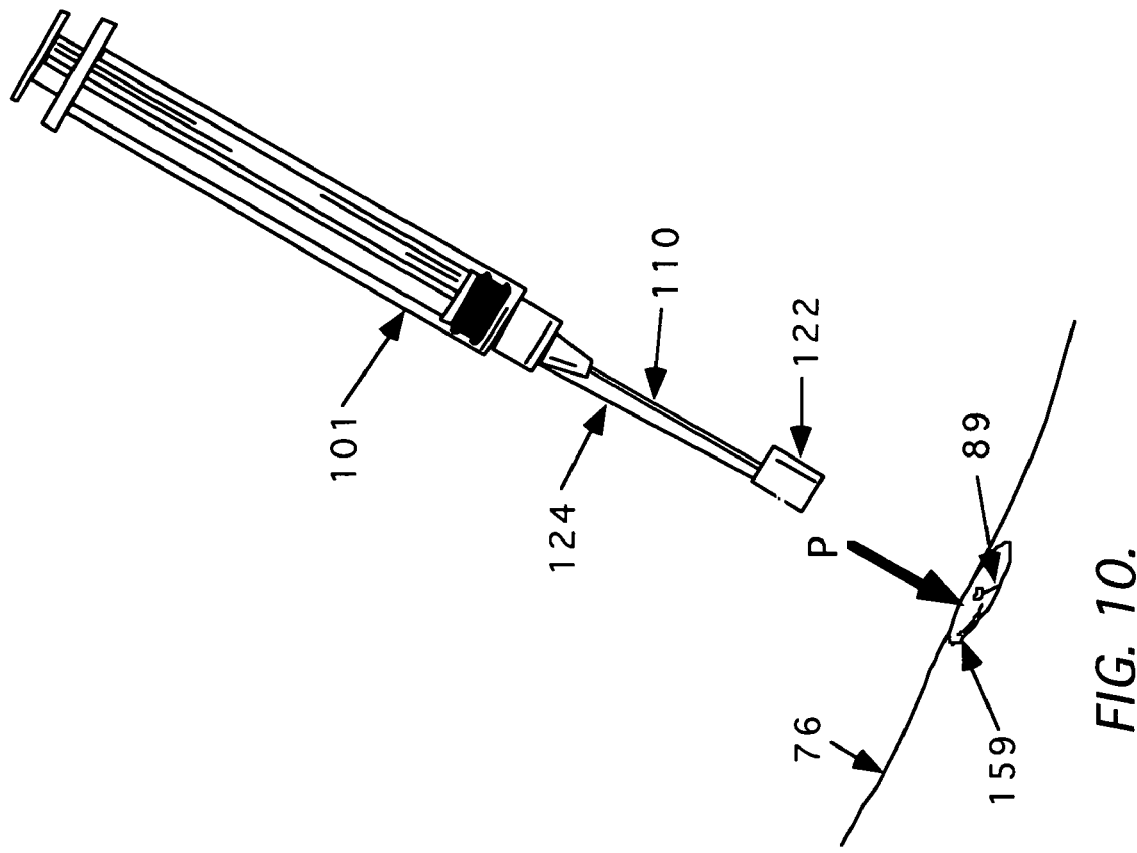
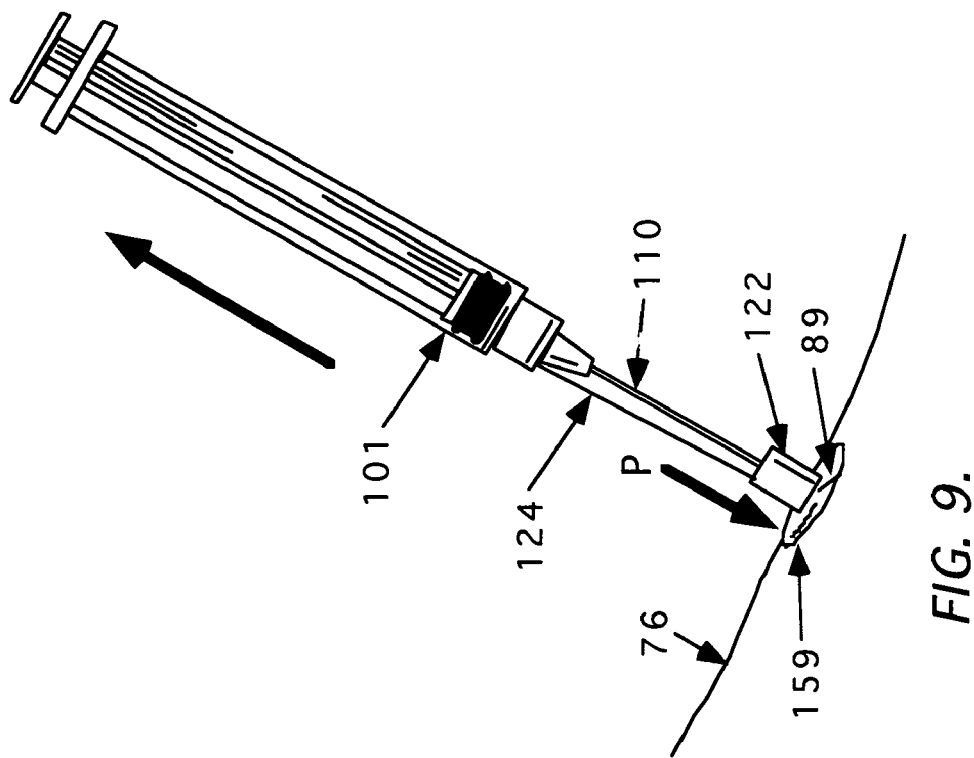

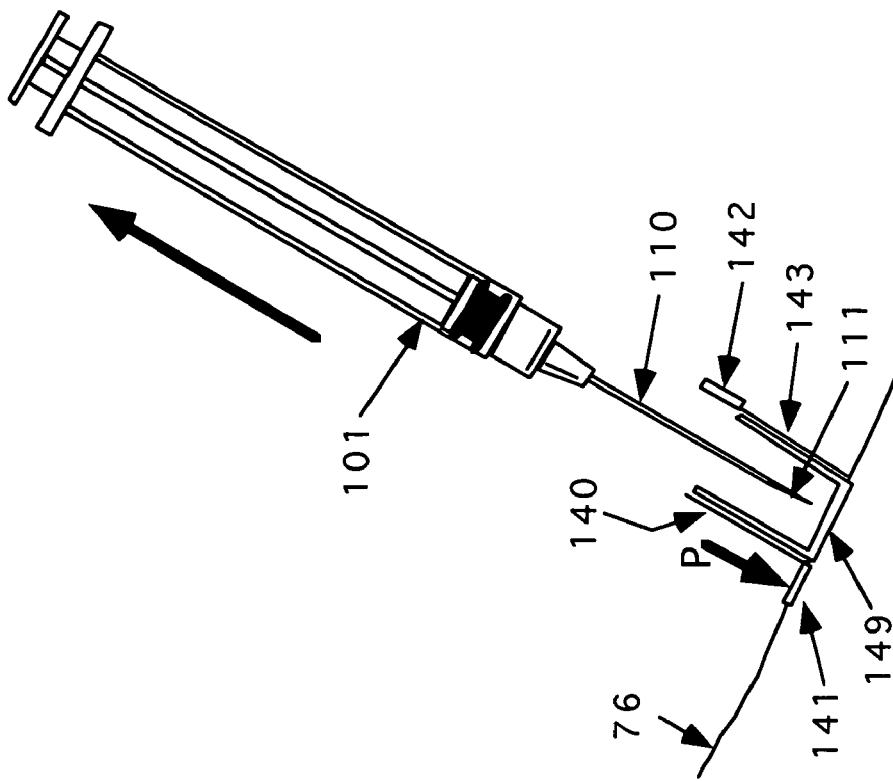
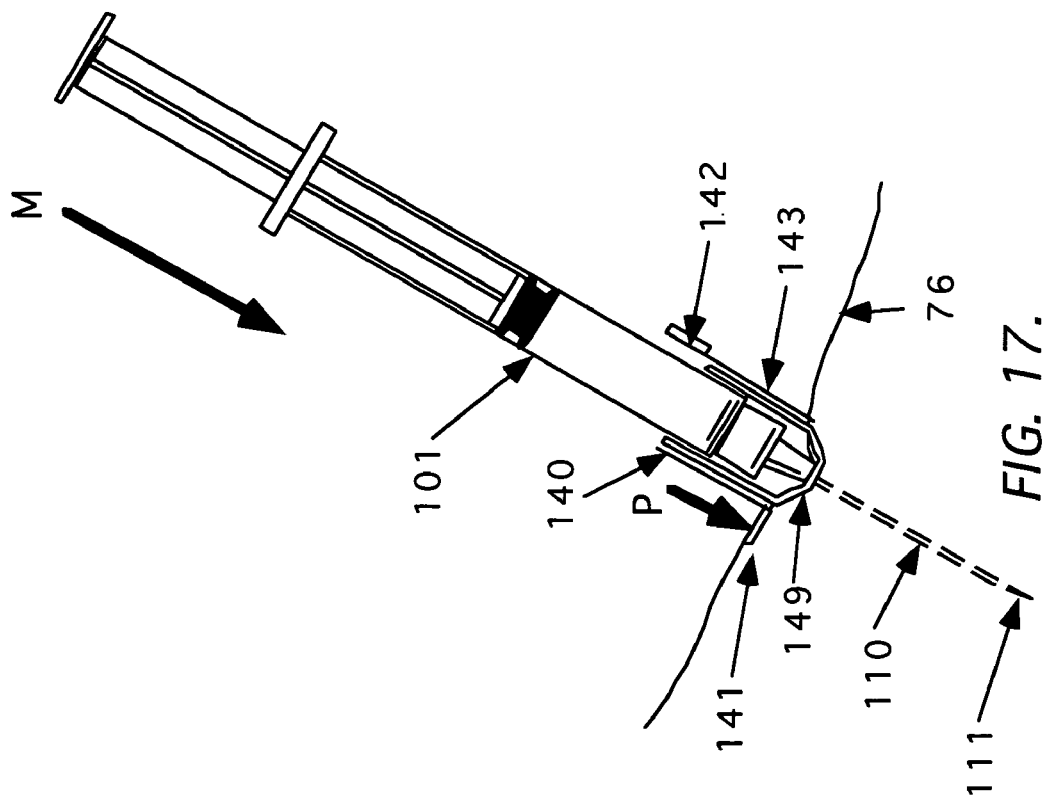
FIG. 17.
FIG. 18.

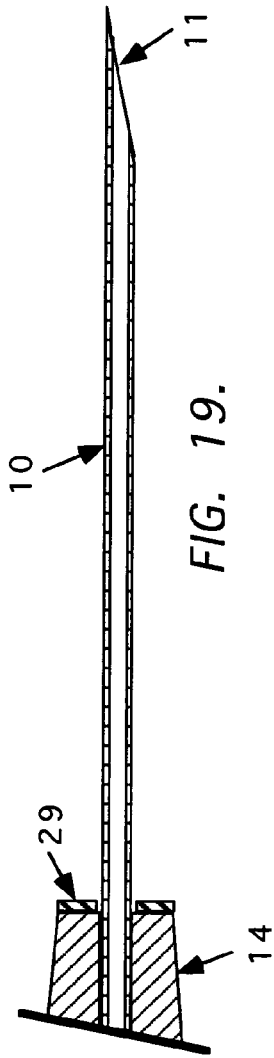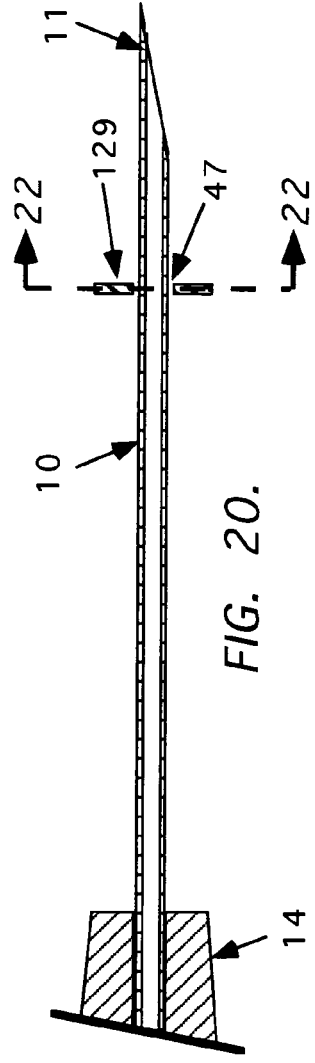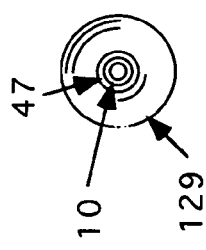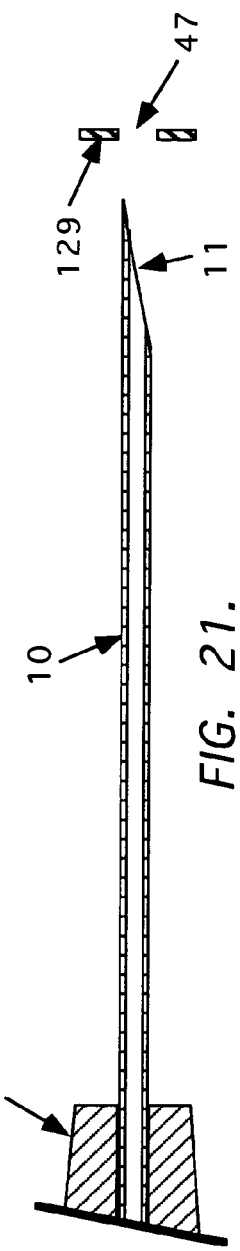

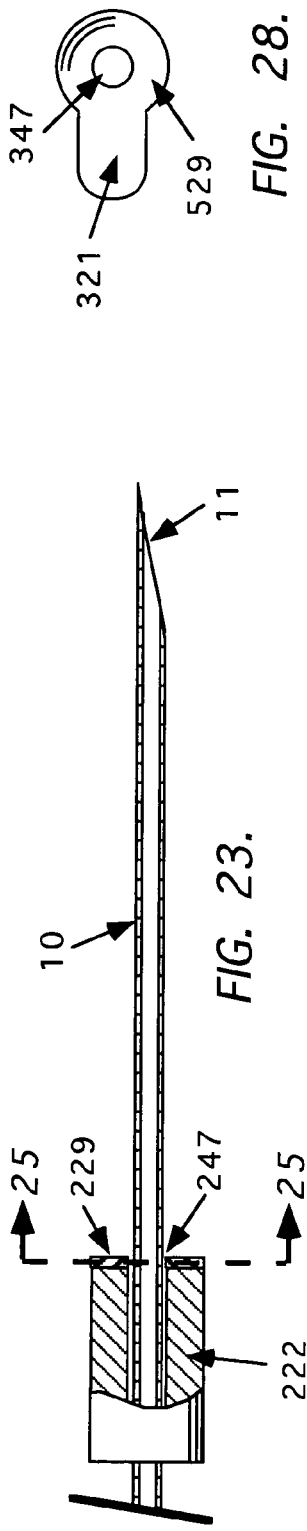
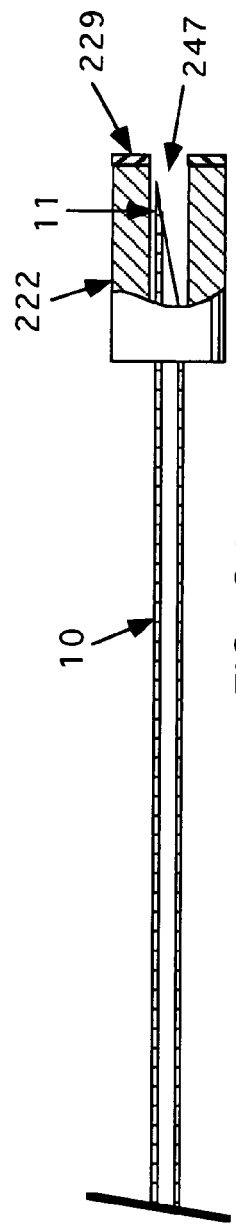
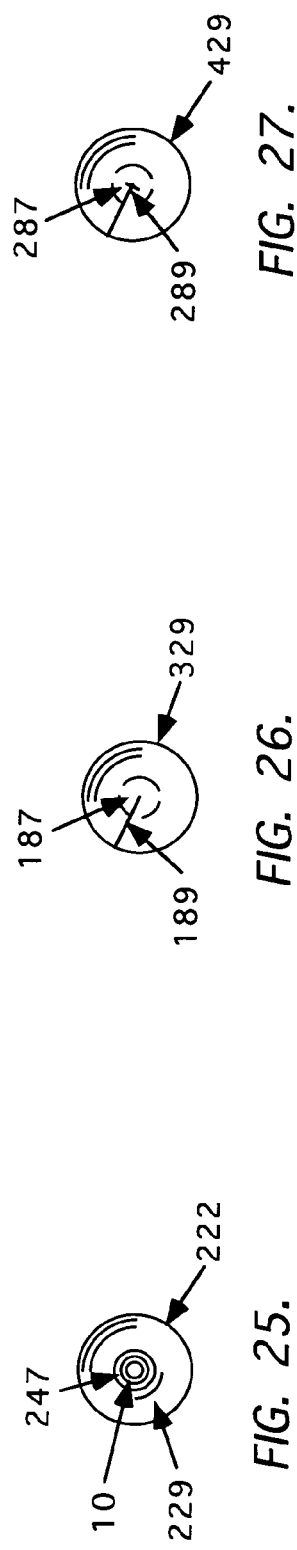
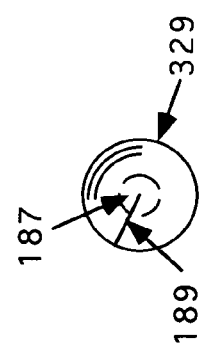

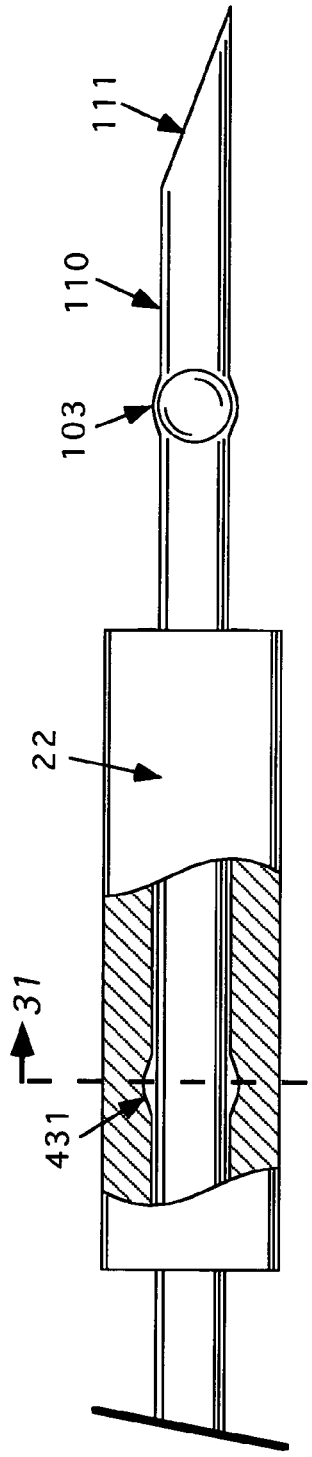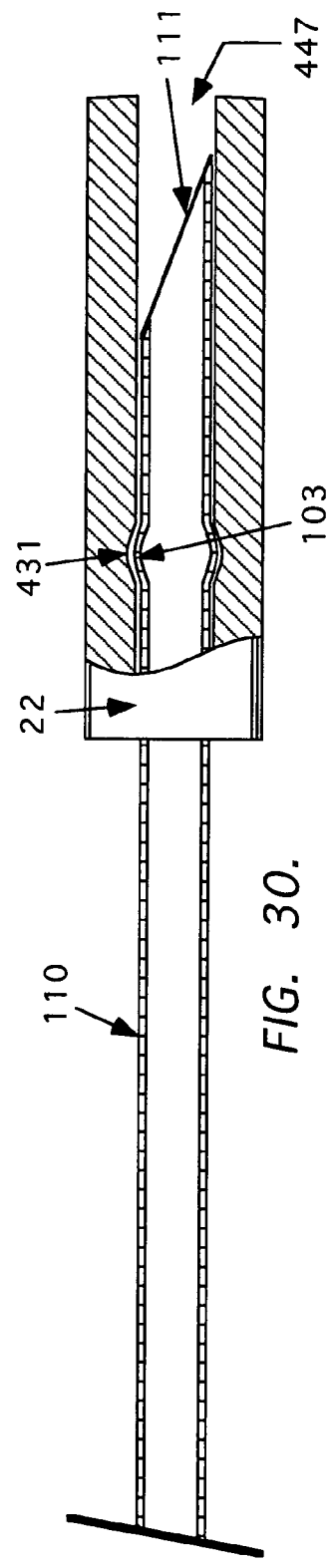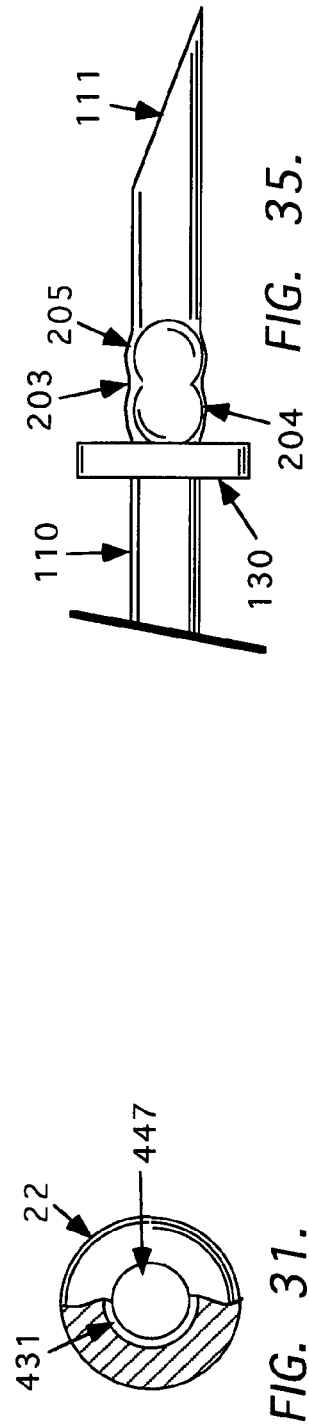

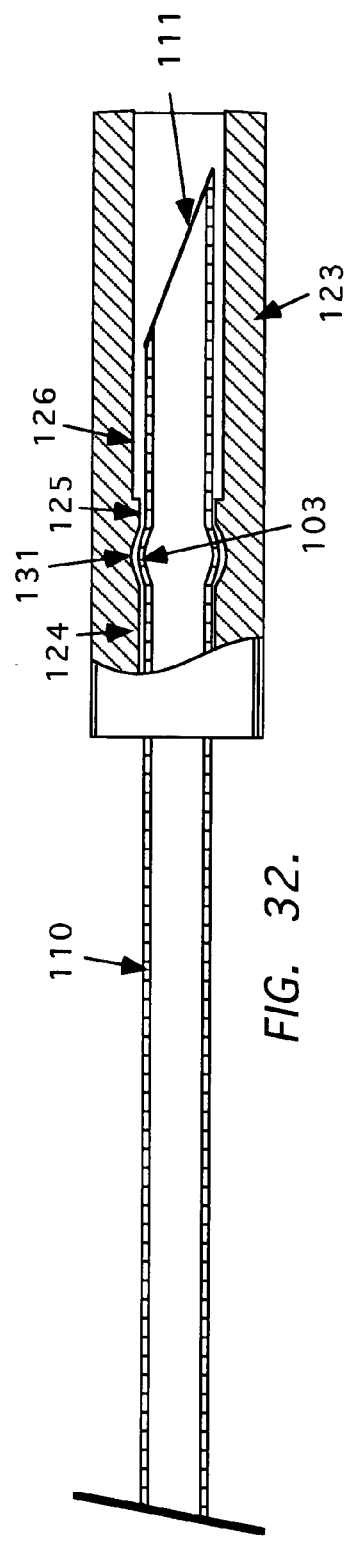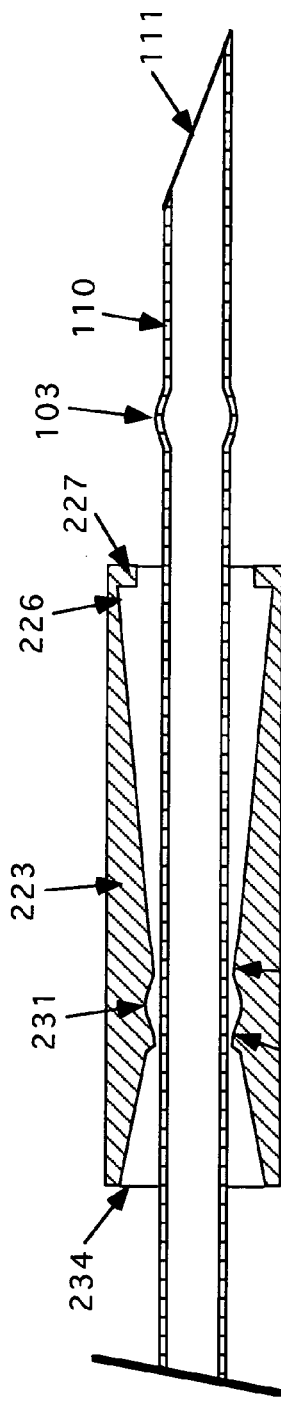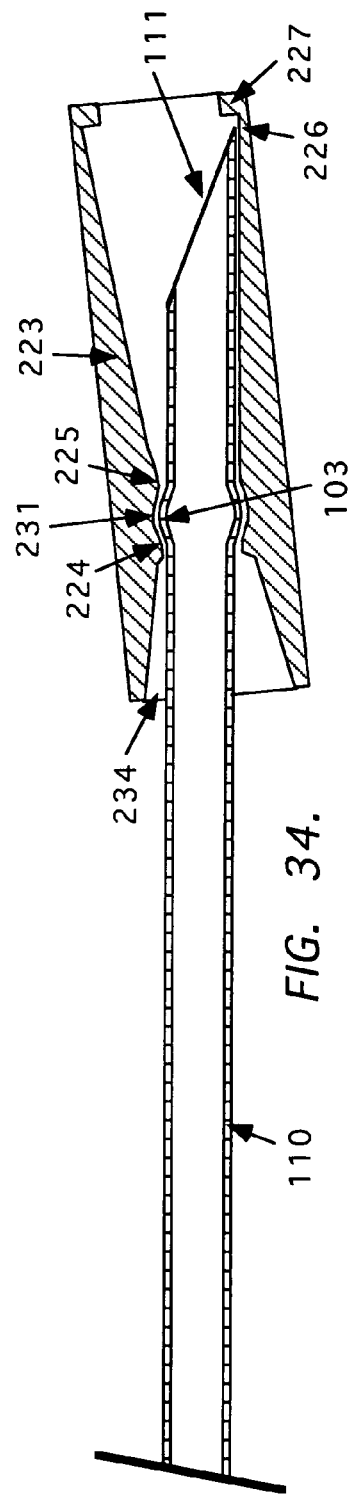

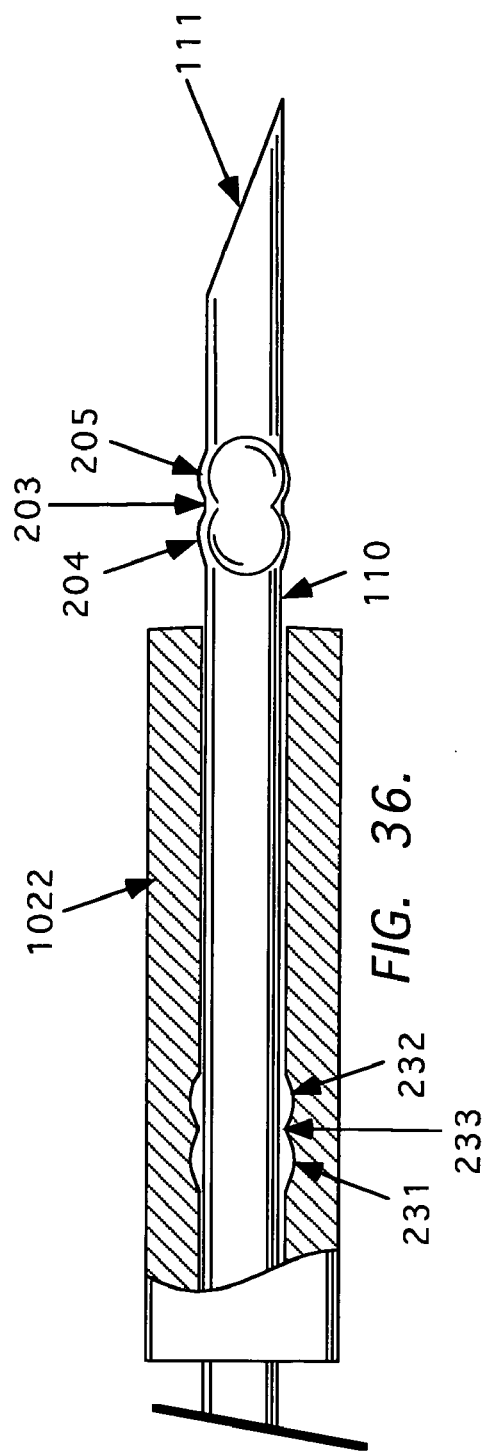
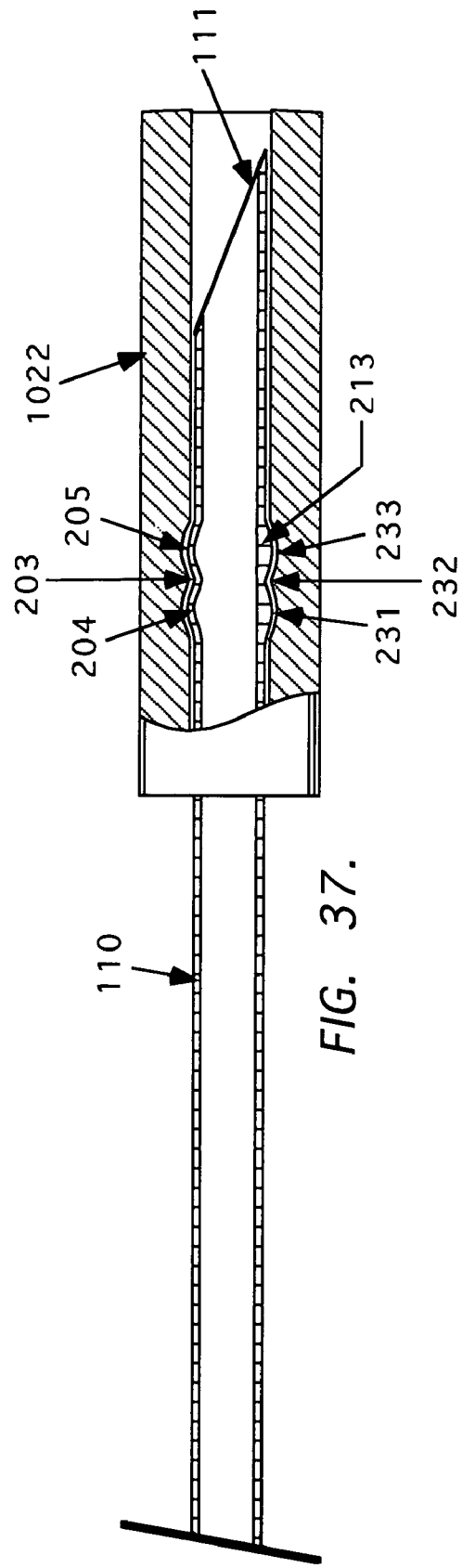
FIG. 36.
FIG. 37.

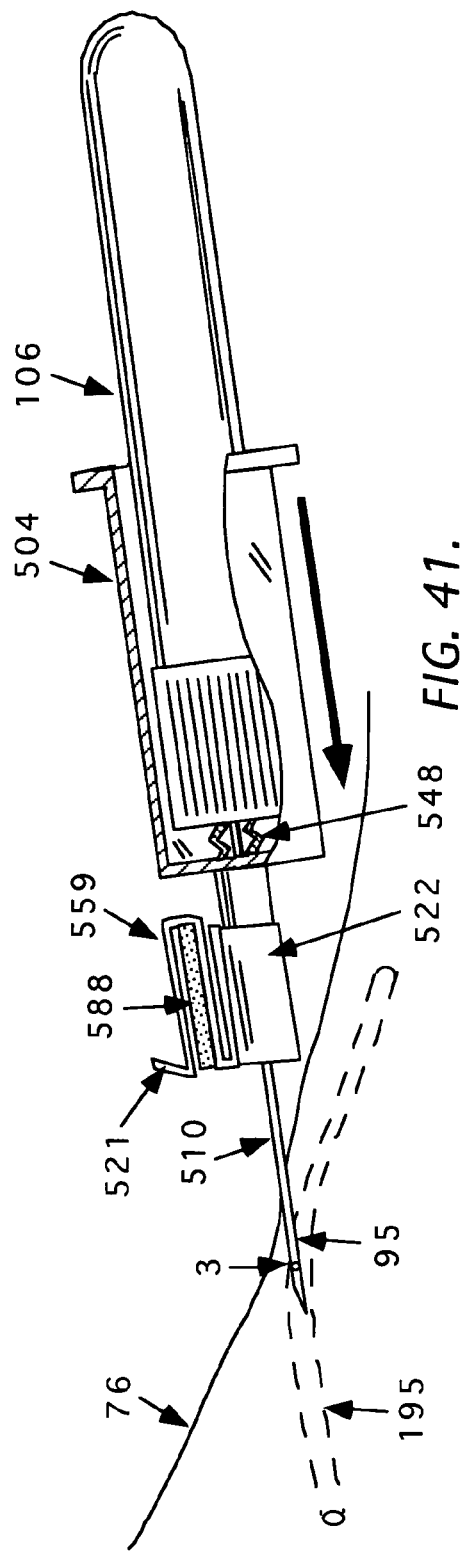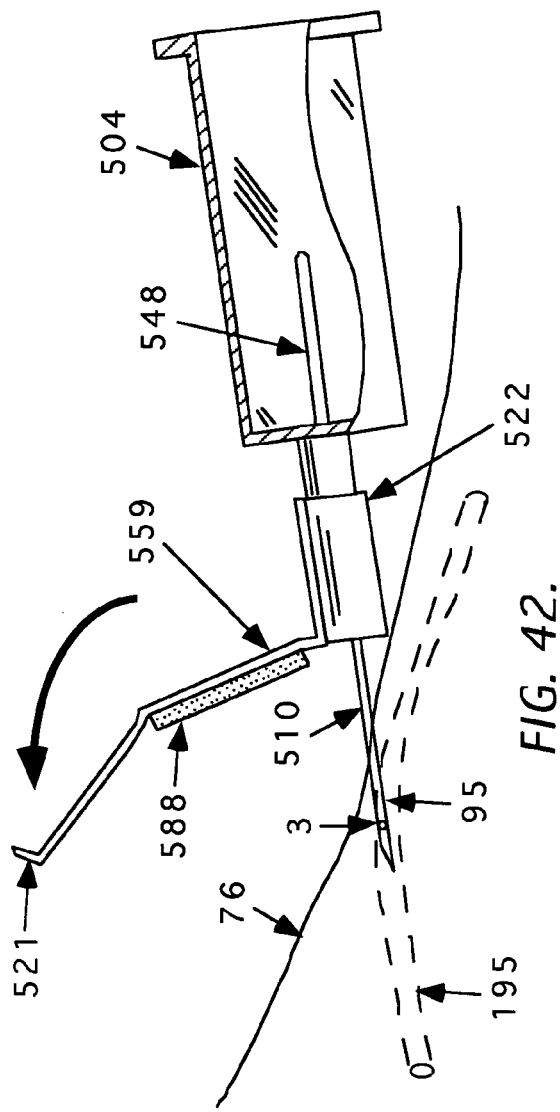
FIG. 41.
FIG. 42.

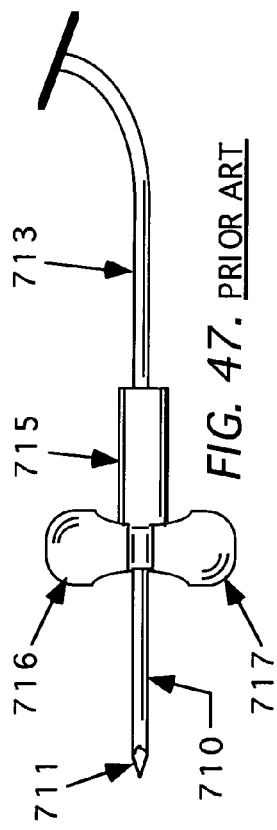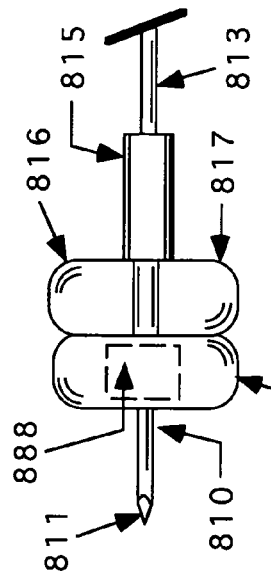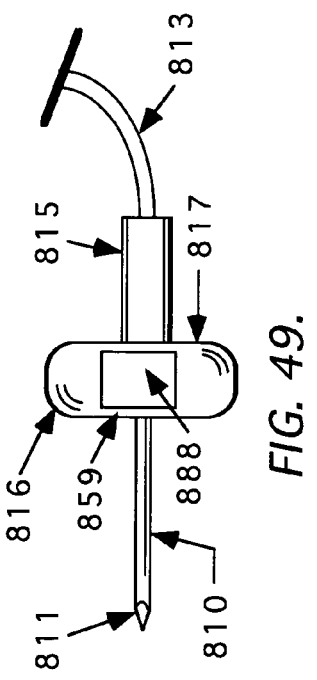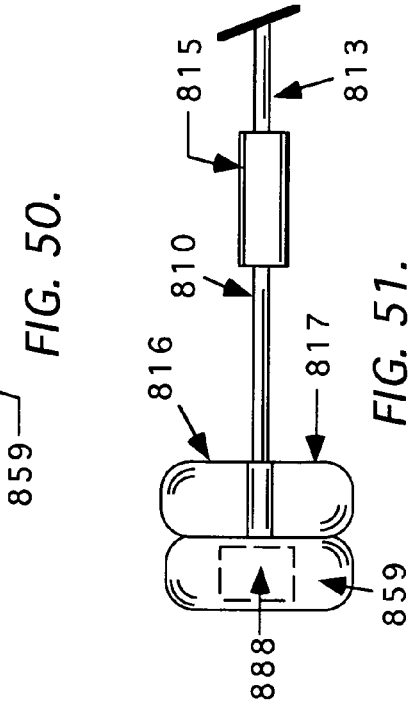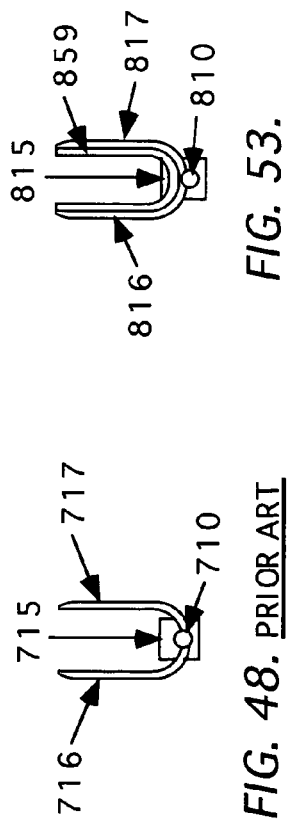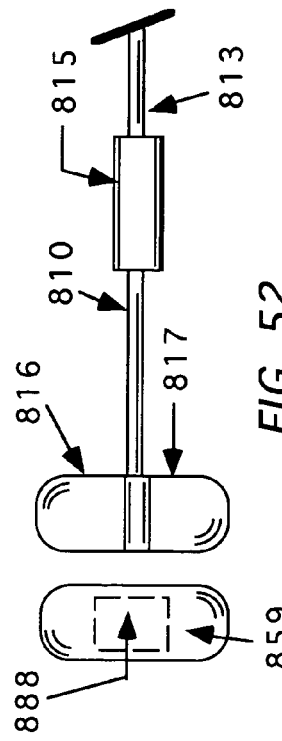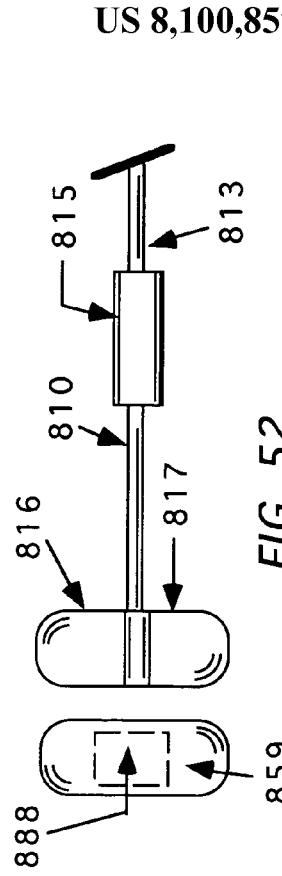

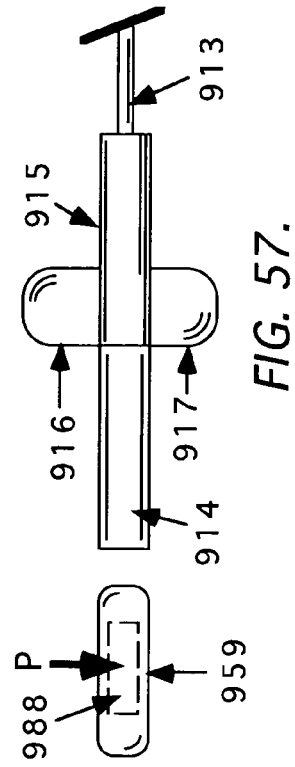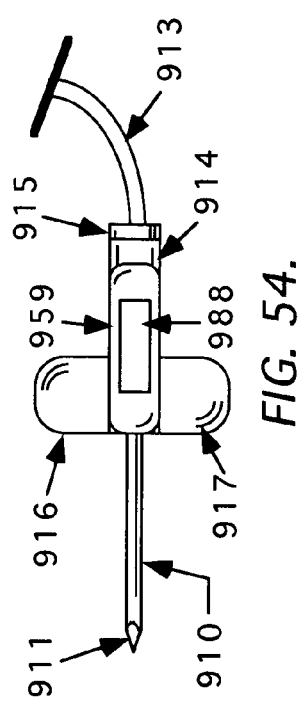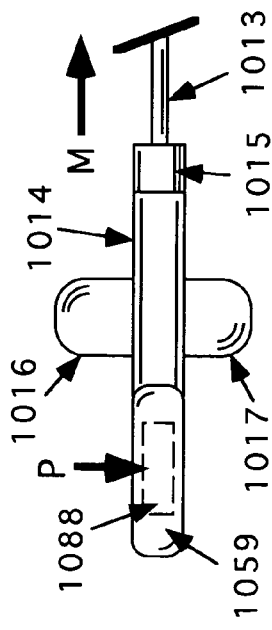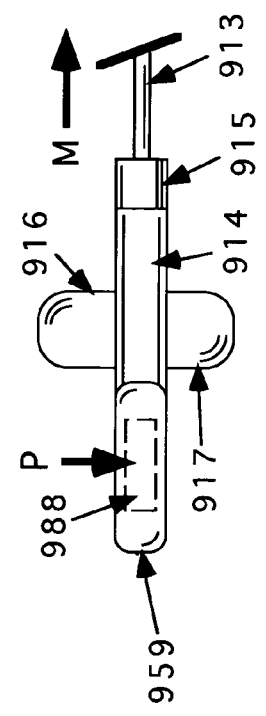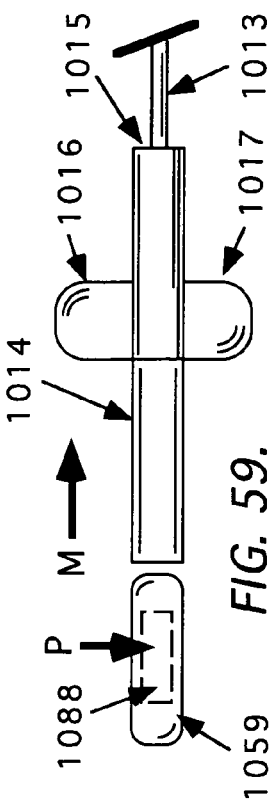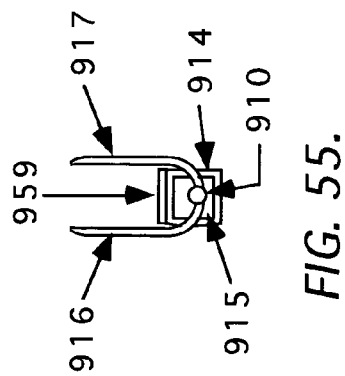

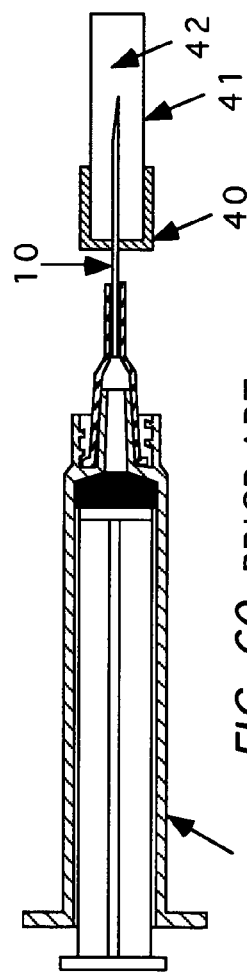
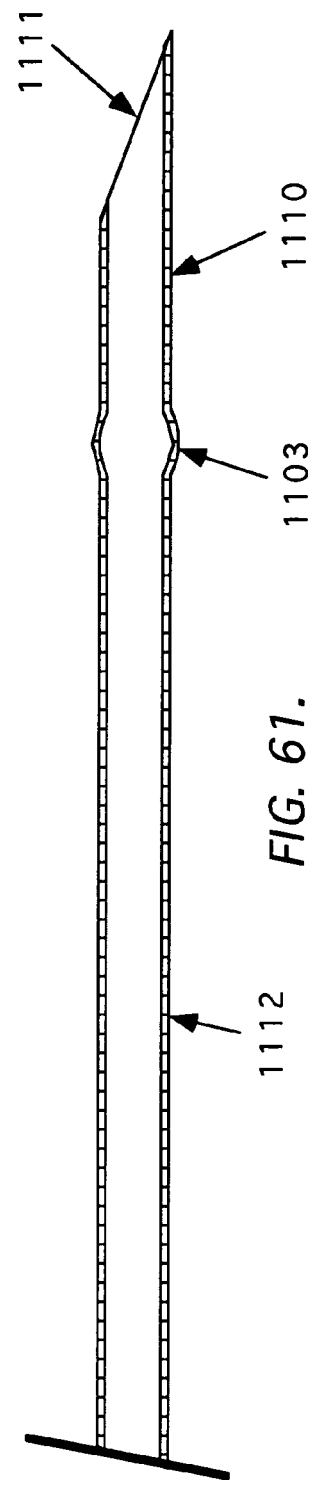
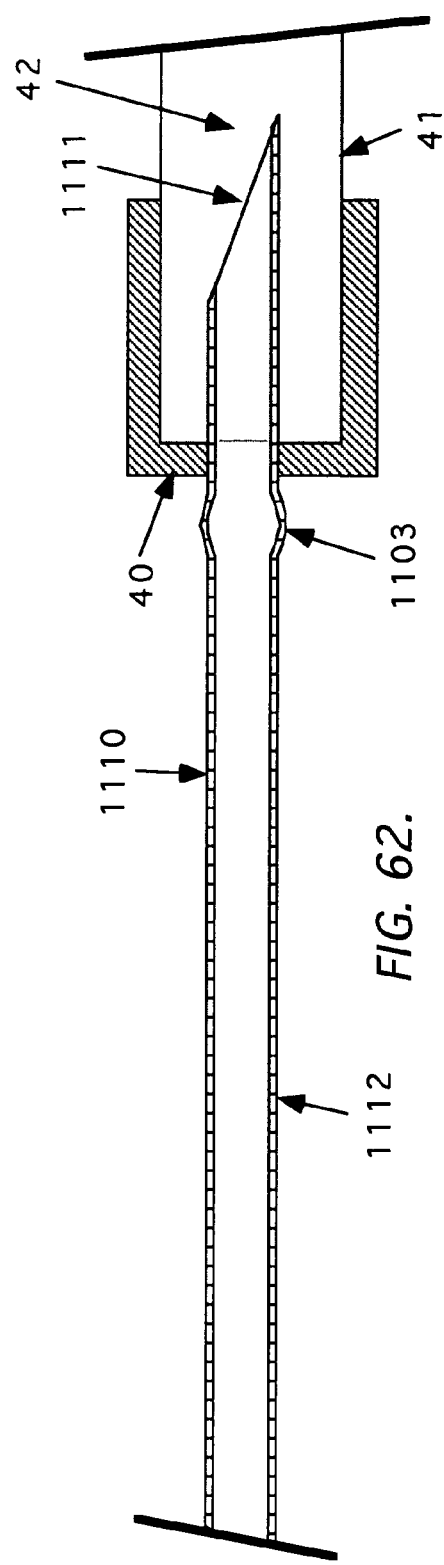
FIG. 60. PRIOR ART
FIG. 61.
FIG. 62.

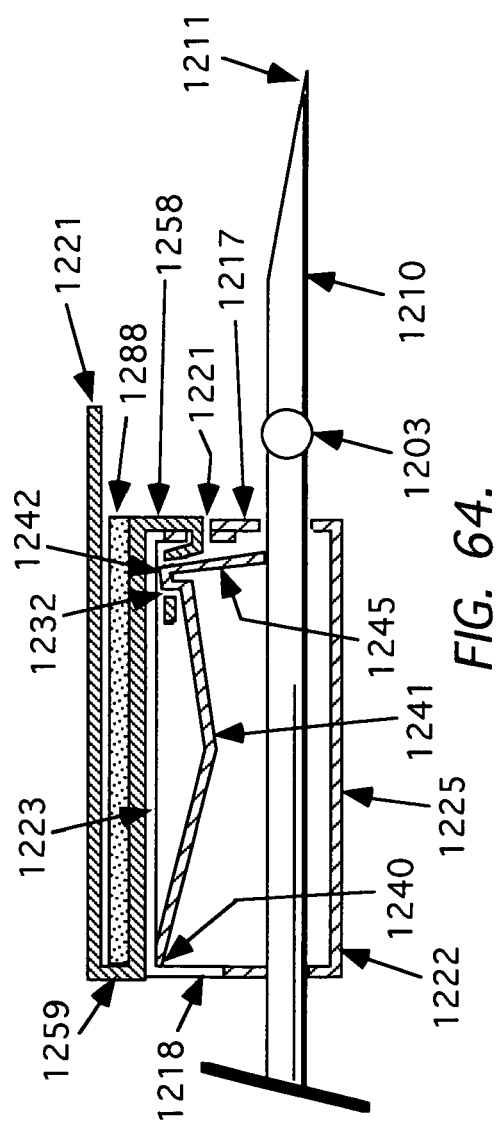
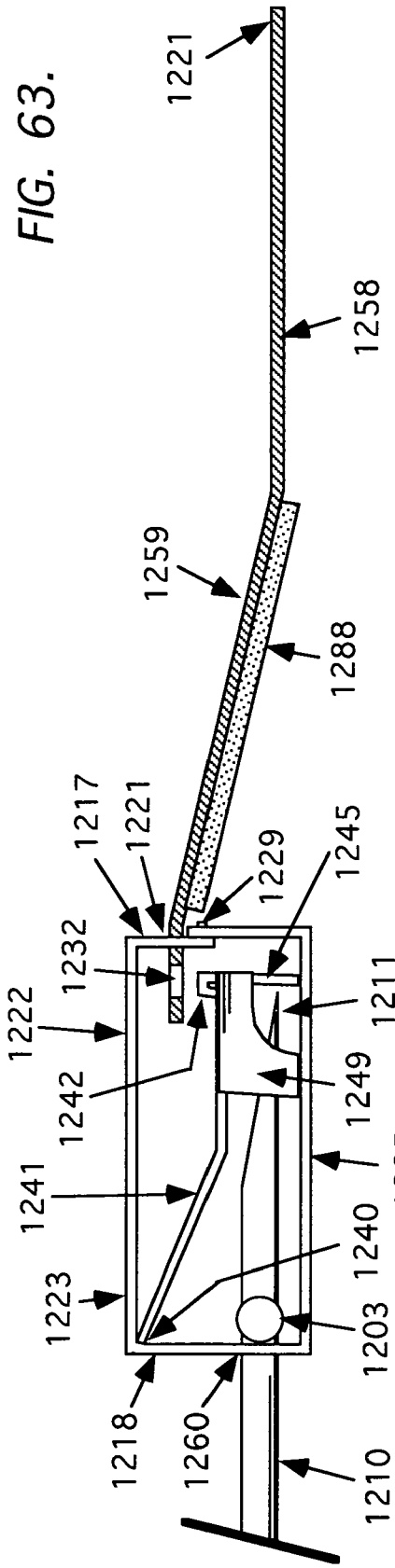
FIG. 63.
FIG. 64.
FIG. 65.

METHOD AND APPARATUS FOR INDICATING OR COVERING A PERCUTANEOUS PUNCTURE SITE

CROSS REFERENCE TO RELATED APPLICATION

This application is related to and claims the benefit of filing date of the following U.S. Provisional Patent Application Ser. No. 60/308,008, entitled METHOD AND APPARATUS FOR INDICATING OR COVERING A PERCUTANEOUS PUNCTURE SITE, filed Jul. 25, 2001, and U.S. patent application Ser. No. 10/206,176, entitled METHOD AND APPARATUS FOR INDICATING OR COVERING A PERCUTANEOUS PUNCTURE SITE, filed Jul. 25, 2002.

STATEMENT RE: FEDERALLY SPONSORED RESEARCH/DEVELOPMENT (Not Applicable)

BACKGROUND OF THE INVENTION

The present invention relates generally to hypodermic needles having a means for indicating or covering a puncture site, and needle protecting devices such as retracting needles and needle guards for hypodermic needles including an apparatus for indicating or covering a puncture site and a means for selectively determining the depth of needle penetration into a vial or tissue.

The dramatic increase in the global proliferation of blood-borne pathogens such as Human Immunodeficiency Virus (HIV), Hepatitis B Virus (HBV), Hepatitis C Virus (HCV), and over twenty more known bloodborne pathogens transmitted via blood and bodily fluids, is having much broader socio-economic ramifications than previously thought. Since the discovery of HIV and resulting Acquired Immunodeficiency Syndrome (AIDS) epidemic, approximately 65 million people have contracted the virus and an estimated 25 million people have died from AIDS-related illnesses. Meaning approximately 40 million individuals are living with HIV, with over 90% of those infected unaware of their infection and able to spread the disease. New data indicates the AIDS epidemic is spreading far more rapidly in the developing world than any global-level disease that preceded it. The epidemiological models previously used to predict the spread of other diseases are proving to be grossly inaccurate and useless. Although 1.3 million people living with AIDS in undeveloped countries have access to antiretroviral drugs, it is estimated that 80% do not have access to treatment. Without massive new intervention, experts predict an additional 70 million people will die from AIDS within the next two decades.

HIV prevalence is now approaching 40% of the population in some Sub-Saharan countries in Africa. New HIV infection rates in China, Indonesia, Latin America, South and Southeast Asia are exploding, with some infection rates increasing 70% in the first six months of 2001. The rate of new infections in the developed world has stabilized, but over 1.5 million are HIV-positive or living with AIDS. The United Nations is calling for unprecedented intervention to stem the growing number of people being infected with HIV.

In addition to the exploding population of those infected with HIV, a significant number of patients being treated with antiretroviral therapy are infected with a virus that has developed a resistance to any of the therapies currently available. In 2001, clinical studies in San Francisco determined that approximately 25% of HIV-positive patients being treated with the first and most widely available drug prophylaxis, reverse transcriptase inhibitors, had a HIV strain that developed drug-resistance within a short time. Researchers also monitored patients receiving the second generation antiviral drugs, non-nucleoside reverse transcriptase inhibitors, reporting no drug-resistant HIV strains in 1996, but were alarmed that 13% of those tested had developed a resistance to this new potent class of drugs. Both of these types of anti-viral drugs are expected to be widely used in the developing world because of cost. Even more alarming is the fact that 7% of HIV-positive patients receiving one of the third generation of antiretroviral drugs, protease inhibitors, also had an HIV strain that had developed a resistance to this treatment.

Additionally, the excitement over the new fourth generation CCR5 receptor antagonist class drugs that target the white blood cells of the immune system and not HIV itself has been tempered because the drugs may accelerate the shift of one variant of HIV to a second variant.

Another huge roadblock to the development of a vaccine or effective drug prophylaxis is the advent of dual HIV infection, where an individual is infected with two distinct HIV strains. The evidence of this phenomenon is the presence of recombinant viruses that include genetic material from two distinct parental HIV strains. The only way recombinant viruses are created is when simultaneous replication occurs between two distinct parental strains in the same patient. Dual infection can occur two ways: coinfection, when the host is infected with two distinct parental viruses at or around the same time, and; superinfection, where a sequential infection of two different viral strains occurs.

The presence of HIV or any of these bloodborne pathogens in patients poses a risk to healthcare workers when invasive, hypodermic procedures are performed. As the population of infected individuals' increases, more people will be treated by healthcare workers, further increasing the odds of disease transmission from patient to healthcare worker. Blood must be collected to determine and monitor the viral load in infected patients. The need for a passive blood collection system is enormous because of the increased demand for blood sampling.

The United States has mandated the use of safety engineered hypodermics in the workplace and many of the currently available safety products are not being well received by clinicians. The design of the great majority of these first generation safety devices requires a change in protocol, and an additional step or action to disable the contaminated hypodermic needle. The retracting syringe needles now available also require an additional step after the medication is administered with a syringe and the clinician is required to exert a significant force on the plunger rod to activate the retracting mechanism of the device. The retracting IV catheter, or the winged infusion needle, also requires the clinician to press a button to retract the needle into the needle hub or holder. One of the most glaring problems of the retracting needles are that they regurgitate the blood or bodily fluid contained in the needle when the needle retracts into the closed syringe, hub or handle. What is needed is a safety hypodermic needle that eliminates exposure time to the contaminated needle and does not harm the patient or caregiver.

The final result of any hypodermic or percutaneous procedure is that the puncture site is covered with a bandage, or wound dressing, after removal of the needle or stylet. The ability to simultaneously cover the puncture site during the procedure, or at the time of needle withdrawal, benefits the patient by reducing the time the wound is exposed to any potential air, skin or fluid-borne contaminants and potential infection, as well as the caregiver, who is now able to address the proper disposal of the contaminated needle without having to attempt to place a bandage or wound dressing, which may require the use of both hands. If a sharps container is not within reach, some caregivers routinely place the barrel of the used syringe in their mouth while placing the bandage over the puncture site.

Although an absorbent material is routinely used both before and after a hypodermic procedure, the existing prior art mostly teaches the use of the absorbent material to apply anesthetic or medication to the puncture site prior to needle insertion. In U.S. Pat. No. 4,799,926, Haber teaches a self-contained, sterile medication applying swab at the proximal end of a syringe plunger which is used prior to the puncture. In U.S. Pat. No. 4,243,035 Barrett also teaches a swab combined with a syringe, but with an integral swab at the distal end of the syringe for use prior to the puncture. Gringras, in U.S. Pat. No. 3,270,743, teaches a means for administering anesthetic from either the proximal end of the syringe, or the distal end of the needle cover. Golden, in U.S. Pat. No. 4,755,170, teaches a slidable, double portioned, cutaneous sealing apparatus, concentrically located about a needle, but does not teach a secure means to prevent the needle tip from being re-exposed after use nor includes a deployable bandage or wound dressing having an automatic peeling release liner. What is needed is a puncture site indicating or covering apparatus that is integral to the hypodermic apparatus, easy to use, includes a deployable bandage or wound dressing with a self-separating release liner and provides protection for both the patient and caregiver.

Some hypodermic needle diameters are so small that it is difficult to tell where the puncture has been made after the needle is withdrawn from the patient. Since a bandage is placed over the puncture site, an indicator marking the puncture site would be helpful to the attending clinician in properly placing the bandage or covering.

A simple needle shaft depth indicator is also disclosed in the present invention. The routine protocol has previously been to draw medication or diluent into a syringe with one needle, then to remove that fill needle from the syringe. A second, fresh, sterile needle is attached to the syringe and used to address the patient and inject the medicine. This protocol is common because each needle shaft is coated with a lubricating film designed to reduce patient discomfort and tissue drag when the needle is inserted into tissue. When the needle is passed through the stopper of the vial to fill the syringe, the lubricating film on the needle shaft is compromised. A small depth indicator near the distal end of the needle would allow the user to only insert a small portion of the needle shaft through the stopper into the vial, leaving the lubricating film intact on the rest of the needle shaft. Clinicians have been trained to visually observe the needle tip for burrs or other irregularities before using the needle on patients.

Hypodermic needles are used in a wide variety of invasive medical procedures with approximately 25 billion units being consumed on an annual basis. Basically, the great majority of hypodermic needles are disposable, intended for a single-use on an individual patient and are provided sterile in a variety of lengths and gauges. Hypodermic needles are normally discarded after a single use into a specially designed, puncture-proof biohazard container. Europe has broadly adopted disposable, single use regulations in light of the presence of Mad Cow disease.

Hypodermic needles are used in medicine, science, veterinary medicine, the biotechnology and pharmaceutical industries, and also in the chemical industry. Medical and veterinary uses range from injecting medication or diluent into a patient or I.V. port, collecting blood, bodily fluids or specimens from patients, placing guidewires, catheters and implanted ports, heart pacemaker leads, brain surgery and nuclear diagnostic medicine as well as a variety of other clinical procedures. The biotechnology and pharmaceutical applications mainly involve research where substances, liquids, gases or compounds are injected, mixed or withdrawn through a membrane or barrier into a specimen or controlled field. Chemical industry applications involve injecting or removing substances, liquids, gases or compounds to or from a specimen or controlled field. In each and every instance, whether medical or industrial, exposed needles pose a danger of injuring the user.

Despite all the obvious dangers associated with the use of exposed hypodermics, and the availability of manually activated safety hypodermic devices, unguarded, exposed hypodermic needles still are readily available and used throughout the industry. Many institutions have evaluated and tested the commercially available safety products and have rejected many of the technologies for a number of reasons.

The basic problem with many of the present day safety hypodermic devices is that they are meant to be manually activated, or in the language of the medical device industry, they are considered "active" devices. They may have safety shields, retractable needles, moveable sheaths or the like; but they generally require the user to complete another procedure to facilitate engagement of the safety mechanism. Although there are a number of retractable needle devices available, the aforementioned clinical issues are a cause for concern, as well as fluid regurgitation problems when the mechanism is activated.

What is needed is a low-cost safety hypodermic apparatus with a universal application that is low in cost, easy to use, and improves safety for both the patient and caregiver and should include a deployable bandage or wound dressing having a self-peeling release liner as an integral part of the safety hypodermic apparatus, reducing the probability of exposing the caregiver, or patient to contaminated hypodermic needles in the workplace.

SUMMARY OF THE INVENTION

It is therefore an object of the present invention to provide an apparatus for indicating the puncture site made by a percutaneous needle or medical instrument.

It is an object of the present invention to provide a puncture site indicator for a hypodermic needle or apparatus.

It is another object of the present invention to provide an apparatus and method for depositing a mark on a surface when a hypodermic apparatus contacts that surface.

It is another object of the present invention to provide a puncture site indicator that is releasably attached or coupled to a hypodermic needle or apparatus.

It is a further object of the present invention to provide a puncture site indicator that is releasably attached or coupled to a hypodermic needle or apparatus with an adhesive.

It is another object of the present invention to provide a puncture site indicator that is releasably attached or coupled to a hypodermic apparatus by mechanical means.

It is a further object of the present invention to provide a puncture site indicator that is releasably attached or coupled to a hypodermic needle or apparatus by frictional means.

It is a another object of the invention to provide a puncture site indicator that is releasably attached or coupled to a hypodermic needle or apparatus by rotational means.

It is another object of the invention to provide a puncture site cover for a hypodermic needle or apparatus.

It is another object of the present invention to provide a puncture site cover that is releasably attached or coupled to a hypodermic needle or apparatus.

It is a further object of the present invention to provide a puncture site cover that is releasably attached or coupled to a hypodermic needle or apparatus by adhesive.

It is another object of the present invention to provide a puncture site cover that is releasably attached or coupled to a hypodermic needle or apparatus by a slidable means.

It is another object of the present invention to provide a puncture site cover that is releasably attached or coupled to a hypodermic needle or apparatus by mechanical means.

It is a further object of the present invention to provide a puncture site cover that is releasably attached or coupled to a hypodermic needle or apparatus by frictional means.

It is another object of the present invention to provide a puncture site cover that is releasably attached or coupled to a hypodermic needle or apparatus by rotational means.

It is a further object of the present invention to provide a puncture site cover that may include an adhesive.

It is one more object of the present invention to provide a puncture site cover that may include an absorbent material.

It is another object of the present invention to provide a puncture site cover that may include an absorbent material that includes an anesthetic, antimicrobial, antibiotic or any other medication used to minimize or reduce infections.

It is a further object of the present invention to provide a puncture site cover that may include an absorbent material that includes a powder.

It is a further object of the present invention to provide a puncture site cover that includes a puncture proof material.

It is also an object of the present invention to provide a needle point guard that effectively shields the sharpened distal tip of the needle after use.

It is another object of the present invention to provide a safety hypodermic apparatus which is automatic and/or semi-automatic covering, fail-safe and single-use in nature.

It is another object of the present invention to provide a safety hypodermic apparatus which looks similar to a standard, exposed, disposable hypodermic needle device (i.e., the needle and needle tip are exposed prior to performing the hypodermic procedure).

It is another object of the present invention to provide a safety hypodermic apparatus which conforms to existing procedures for aspirating medication into a syringe, administering injections, and allowing unrestricted access for vascular access or catheter insertion.

It is yet another object of the present invention to provide a safety hypodermic apparatus which provides an exposed sharpened tip for bevel-up needle viewing.

It is a further object of the present invention to provide a safety hypodermic apparatus which allows medication or diluent to be aspirated into a syringe without prematurely activating the automatic and/or manually covering safety mechanism.

It is a still further object of the present invention to provide a safety hypodermic apparatus which can be used with a double lancet needle for piercing a cartridge in a pre-filled syringe, or a stopper in a blood collection vacuum tube.

It is an additional object of the present invention to provide a safety hypodermic apparatus which lends itself to automated manufacturing.

It is yet another object of the present invention to leave the delicate, sharpened needle tip untouched during assembly procedures, ensuring the sharpest needle tip possible to minimize any patient discomfort during use of the hypodermic device.

It is a further object of the present invention to reduce the number of components to the lowest possible number needed to accomplish the intended task of providing acceptable, low cost, fail-safe, single-use hypodermic devices for the healthcare industry.

It is another object of the present invention to provide a safety hypodermic apparatus that includes a retaining means that may include a gripping means.

It is an object of the invention to provide a safety hypodermic apparatus that includes a means for receiving and limiting a slidable member at the distal end of a hypodermic needle or apparatus.

It is another object of the present invention to provide a safety hypodermic apparatus that includes a means for limiting the axial movement and receiving a member near the distal end of a hypodermic needle or apparatus.

It is a further object of the present invention to provide a safety hypodermic apparatus that includes a means for confining an expanded portion of a shaft of a hypodermic needle or apparatus within a sliding member.

It is another object of the present invention to provide a safety hypodermic apparatus that includes a means for confining a sliding member on an expanded portion of a shaft of a hypodermic needle.

It is yet another object of the present invention to provide a safety hypodermic apparatus that includes a means for wedge impacting a sliding member on an expanded portion of a shaft of a hypodermic needle.

It is yet a further object of the present invention to provide a safety hypodermic apparatus that includes a means for binding a sliding member on the distal end of a hypodermic needle.

It is yet a further object of the present invention to provide a safety hypodermic apparatus that includes a means for clamping a sliding member on the distal end of a hypodermic needle.

It is yet one more object of the present invention to provide a safety hypodermic apparatus that includes a means for limiting the axial movement of a sliding member on an expanded portion of a shaft of a hypodermic needle.

It is another object of the present invention to provide a safety hypodermic apparatus that includes a slidable housing that is releasably retained at the proximal end of a hypodermic needle.

It is yet another object of the present invention to provide a safety hypodermic apparatus that includes a slidable housing that is selectively releasable to axially slide on a hypodermic needle.

It is another object of the present invention to provide a safety hypodermic apparatus that includes a visual indicator to show the limited penetration of needle through a stopper, port or into tissue.

It is another object of the present invention to provide a safety hypodermic apparatus that includes a deployable bandage having an automatic peeling release liner where no additional step is required to secure wound dressing to a puncture site when a percutaneous procedure is performed.

It is a another object of the present invention to provide a safety hypodermic apparatus that can be formed from as single sheet, flat or plate of material.

It is a further object of the present invention to provide a safety hypodermic apparatus that can be formed from as single sheet, flat or plate of material and includes a movable needle trap.

It is another object of the present invention to provide a safety hypodermic apparatus that includes a needle guard having a movable needle trap with a means to retain a releasable member or bandage that includes an automatic peeling release liner, said bandage being mechanically attached to the protective needle guard until the sharpened tip of the hypodermic needle is securely covered.

It is another object of the present invention to provide a safety hypodermic apparatus that can be formed from as single sheet, flat or plate of material and includes a movable, lockable needle trap having a means to retain a releasable member or bandage that is mechanically attached to the needle trap until the sharpened tip of the hypodermic needle is securely covered.

In one embodiment, a puncture site indicator may be included with a hypodermic needle or the like. When a needle is inserted in the tissue, a needle hub with a puncture site indicator contacts the tissue, a fluid or the like is released marking or indicating the puncture site location that may include a dye, a coloring, a pigment, an anesthetic, antimicrobial, antibacterial, or other medication or ointment. The fluid may also be dissolvable or absorbable. In another embodiment, a puncture site cover is included on a hypodermic apparatus and is deployable onto the puncture site. The puncture site cover may be releasably coupled to a needle guard, and may be deployable in the course of performing the procedure. Essentially, combining a hypodermic needle guard and a puncture site cover is analogous to the procedure trays widely used in the medical industry because all the elements needed to perform the procedure are integrated into the apparatus.

In another embodiment, a hypodermic needle is attached to a housing or hub. A coil spring may be positioned between the hub, or housing. The spring provides the biasing force for advancing the housing or hub forward along the shaft of the needle to the distal end.

In yet another embodiment, the housing or hub may include a slidable washer or bushing that engages a change in profile at a location on a needle.

In another embodiment, a needle with a change in profile limits the axial movement of a sliding member that includes a chamber or cavity for receiving a change in profile on a needle. In one embodiment, at least one change in profile is on the needle. In another embodiment, a plurality of change in profiles are on the needle. In one embodiment, the change in profile may be wedge impacted in a sliding member when the sliding member engages the change in profile. The change in profile may also become confined within a sliding member when a change in profile of the needle is received by a sliding member having a chamber with a similar shape as the change in profile where the axial movement of the sliding member is restricted or limited.

In another embodiment, when a needle is inserted in the tissue, a puncture site indicator may be released and remain in contact with the skin as the needle is removed. The puncture site indicator may include an adhesive on at least one surface. It may be preferable to have adhesive on the surface that contacts the hypodermic apparatus and the surface that contacts the skin. The adhesive bond may be greater when the puncture site indicator contacts the skin, relative to the adhesive strength of the puncture site indicator contacting the hypodermic apparatus. This would allow the puncture site indicator to remain attached to the skin during needle withdrawal without placing pressure on the puncture site indicator. The puncture site indicator may also include an absorbent material that may include a dye, a coloring, an anesthetic, antimicrobial, antibacterial, or other medication or ointment.

In yet another embodiment, a hypodermic apparatus includes a releasable member for covering a puncture site during insertion into tissue, during the procedure, or during removal from tissue. The member may include adhesive for maintaining the member on a puncture site during insertion, during the procedure or as the needle is removed from the tissue. The puncture site cover may also include a puncture-proof material or armor. The needle protective apparatus may also include a needle guard having a movable and needle trap with a means to retain a releasable member or bandage that includes an automatic or self peeling release liner, said bandage being mechanically attached to the protective needle guard until the sharpened tip of the hypodermic needle is securely locked and covered by the movable needle trap. A dye, a coloring, an anesthetic, antimicrobial, antibacterial, or the like may also be included on or in the puncture site covering.

In another embodiment, a hypodermic apparatus includes a releasable member for covering a puncture site during insertion in tissue, or during or after removal from tissue. The member may include adhesive for maintaining the member on a puncture site during insertion, or as or after the needle is removed from the tissue. The puncture site cover may also include a puncture-proof material or armor. The puncture site cover may also include an absorbent material that absorbs any blood or fluids that are present as a result of the procedure. A dye, a coloring, an anesthetic, antimicrobial, antibacterial, or the like may also be included on or in the puncture site covering.

In another embodiment, a needle guard formed from a single sheet or plate of material is disclosed, including progressive steps necessary to manufacture the present invention. The guard may be stamped, heat formed and may comprise metal, plastic resin or a blend of materials suitable for forming and safely covering a hypodermic needle after use. This embodiment also lends itself to injection molding manufacture.

In another embodiment, a penetration depth indicator may be included on a needle, preventing the lubricating film on the needle from being compromised when filling a syringe.

Other objects and benefits of this invention will become apparent from the description which follows hereinafter when read in conjunction with the figures that accompany it.

BRIEF DESCRIPTION OF THE DRAWINGS

These as well as other features of the present invention will become more apparent upon reference to the drawings wherein:

FIG. 1 is a full side view of a prior art needle and syringe inserted into tissue.

FIG. 2 is a full side view of the prior art needle and syringe of FIG. 1 with the syringe and the needle fully removed from the puncture site, and a bandage being placed on the puncture site.

FIG. 3 is a full side view of the prior art needle and syringe of FIGS. 1 and 2 with the syringe and the needle fully removed from the puncture site and a bandage covering the puncture site.

FIG. 4 is a full side view of the hypodermic apparatus of the present invention where the syringe and/or needle includes a puncture site indicator at the proximal end of the needle, distal end of the apparatus, that marks the puncture site during the procedure.

FIG. 5 is a full side view of the hypodermic apparatus of FIG. 4 showing the syringe being withdrawn from the puncture site that is indicated by a mark left on the skin or surface.

FIG. 6 is a full side view of the hypodermic apparatus of the present invention showing fluid being administered by a syringe, the needle inserted in tissue, and a puncture site cover contacting the surface of the skin.

FIG. 7 is a full side view of the hypodermic apparatus of FIG. 6 showing the syringe being withdrawn from the tissue that is now covered with a bandage or detachable member that is releasably attached to a needle housing.

FIG. 8 is a full side view of the hypodermic apparatus of FIGS. 6 and 7 showing the syringe fully withdrawn from the tissue that is covered with a bandage or removable member that is now released from a needle housing.

FIG. 9 is a full side view of the hypodermic apparatus of the present invention showing the syringe being withdrawn from the tissue that is covered with a bandage or detachable member that is releasably attached to the needle housing, with a tether limiting the axial movement of the needle housing along needle.

FIG. 10 is a full side view of the hypodermic apparatus of FIG. 9 showing the syringe fully withdrawn from the tissue that is covered with a bandage or removable member that is now released from the needle housing, with a tether limiting the axial movement of the needle housing along needle.

FIG. 17 is a full side view of the hypodermic apparatus of the present invention showing fluid being administered by a syringe having a needle with a puncture site cover with the needle inserted in tissue.

FIG. 18 is a full side view of the hypodermic apparatus of FIG. 17 showing the needle fully removed from the puncture site and the detachable member or bandage ready to be attached to the surface adjacent to the puncture site. The bandage may include a protrusion at the distal end, or a protrusion at the proximal end.

FIG. 19 is a cross sectional side view of the hypodermic apparatus of the present invention comprising an apparatus having a means for marking or indicating a puncture site.

FIG. 20 is a cross sectional side view of the needle of the present invention showing a slidable member for marking or indicating a puncture site shown at a position along the needle.

FIG. 21 is a cross sectional side view of the needle of FIG. 20 showing a member for marking or indicating a puncture site removed from the distal end of the needle.

FIG. 22 is a full front view of the removable puncture site indicator of FIGS. 20 and 21 along axis 22-22 comprising a slidable member having an aperture with a needle therethrough.

FIG. 23 is a cross sectional side view of a needle with a cut away side view of a sliding member having a member, shown in a cross sectional view, for marking or indicating a puncture site.

FIG. 24 is a cross sectional side view of the needle of FIG. 23 having a slidable member with a puncture site marker or indicator shown near the distal end of the needle.

FIG. 25 is a full front view of the present invention of FIG. 23 in axis 25-25 comprising a needle and a slidable member with a means for marking or indicating a puncture site.

FIG. 26 is a full top view of a member or bandage with an absorbent member or portion and a slit. Bandage may include an absorbent material, shown on the underside of the bandage in broken lines.

FIG. 27 is a full top view of a member or bandage with an absorbent member or portion with another embodiment of a slit. Bandage may include an absorbent material, shown on the underside of the bandage in broken lines.

FIG. 28 is a full top view of a puncture site indicator having an aperture and tab or protrusion. Tab may be folded over to cover aperture.

FIG. 29 is a full side view of a needle having a sliding member located on the needle shaft, said needle having a change in profile near the distal tip of said needle to limit axial movement of said sliding member, and a cut away side view of said sliding member having an inner chamber or cavity.

FIG. 30 is a cross-sectional side view of the needle of FIG. 29 with the sliding member locked at the distal end of the needle, said member covering the sharpened needle tip. The change in profile of the needle shaft and distal needle tip are confined within the inner chamber or cavity of the sliding member that is shown in a cut away side view.

FIG. 31 is a cut away front view of the sliding member of FIGS. 29 and 30 along axis 31-31 comprising a body, an aperture and an inner chamber or cavity.

FIG. 32 is a cross-sectional side view of the present invention with the sliding member locked at the distal end of the needle, said member including an enlarged distal aperture or chamber and covering the sharpened needle tip.

FIG. 33 is a cross-sectional side view of another embodiment of the present invention with the sliding member located on said needle, said member having enlarged proximal and distal portions or chambers, and a needle having a change in profile near the distal end of said needle to limit axial movement of said sliding member.

FIG. 34 is a cross-sectional side view of FIG. 33 with the sliding member with locked at the distal end of the needle, said sliding member being capable of moving off-axis of the needle.

FIG. 35 illustrates a full side view of a needle having an elongated change in profile, or a plurality of changes in profile near the sharpened needle tip with a sliding bushing or washer on the needle.

FIG. 36 is a full side view of a needle and a cut away view of a needle housing of the present invention illustrating a needle having an elongated change in profile near the sharpened needle tip with a sliding member on the needle shaft.

FIG. 37 is a cross-sectional side view of the needle of FIG. 36 with the sliding member locked at the distal end of the needle on an elongated change in profile, that may include a recess or enlargement, said member extending over the sharpened needle tip.

FIG. 41 is a full side view of the passive blood or fluid collection method and apparatus of the present invention comprising a needle holder, a vacuum tube, a double ended needle inserted into a blood vessel, a needle guard and a deployable member or bandage.

FIG. 42 is a full side view of the fluid collection method and apparatus of FIG. 41 showing a slidable member with a needle in a blood vessel and a bandage being deployed over the puncture site.

FIG. 47 is a full top view of a prior art winged infusion or "butterfly" needle apparatus.

FIG. 48 is a full frontal view of a prior art winged infusion or "butterfly" needle apparatus shown in FIG. 47 with the plurality of flexible protrusions or wings on the hub body being bent or folded approximately 90° relative to the needle axis.

FIG. 49 is a full top view of a passive winged infusion or "butterfly" needle apparatus of the present invention including a deployable member, unfoldable from a first position, and releasably coupled to the flexible wings.

FIG. 50 is a full top view of a winged infusion or "butterfly" needle apparatus of FIG. 49 with the deployable member or bandage now folded or moved to a second position covering the puncture site.

FIG. 51 is a full top view of a winged infusion or "butterfly" needle apparatus of FIGS. 49 and 50 with the deployable member or bandage covering the puncture site and the needle and hub being moved axially away from said puncture site and flexible wings.

FIG. 52 is a full top view of a winged infusion or "butterfly" needle apparatus of FIGS. 49-51 with the deployable member or bandage covering the puncture site, now safely separated from said apparatus.

FIG. 53 is a full frontal view of the passive winged infusion or "butterfly" needle apparatus of FIGS. 49-52 having plurality of flexible protrusions or wings, on the hub body, being bent or folded approximately 90° relative to the needle axis.

FIG. 54 is a full top view of another embodiment of the passive winged infusion or "butterfly" needle apparatus of the present invention comprising a deployable member in a first position and releasably coupled to a sliding sleeve member.

FIG. 55 is a full frontal view of the passive winged infusion or "butterfly" needle apparatus of FIG. 54 having plurality of flexible protrusions or wings, on the hub body, being bent or folded approximately 90° relative to the needle axis.

FIG. 56 is a full top view of a winged infusion or "butterfly" needle apparatus of FIGS. 54 and 55 with the deployable member or bandage now unfolded or moved to a second position covering the puncture site, yet still releasably coupled to the sliding sleeve hub body.

FIG. 57 is a full top view of a winged infusion or "butterfly" needle apparatus of FIGS. 54-56 with the deployable member or bandage covering the puncture site, now safely separated from said sliding sleeve apparatus.

FIG. 58 is a full top view of another embodiment of the winged infusion or "butterfly" needle apparatus of the present invention having a slidable deployable member or bandage now moved to a second position covering the puncture site.

FIG. 59 is a full top view of a winged infusion or "butterfly" needle apparatus of FIG. 58 with the deployable member or bandage covering the puncture site, now safely separated from said sliding sleeve apparatus.

FIG. 60 is a full side view of a prior art hypodermic needle puncturing a stopper of a vial.

FIG. 61 is a full side view of a hypodermic needle of the present invention with a depth indicator formed on the needle.

FIG. 62 is a full side view of the hypodermic needle shown in FIG. 61 shown penetrating a stopper of a medicine vial.

FIG. 63 is a full bottom view of a bandage with an adhesive coated surface, an absorbent area and an aperture for releasably attaching said bandage to a needle guard.

FIG. 64 is a full side view of an exposed, ready to use hypodermic needle and a partial cutaway view of a slidable needle guard having a movable needle trap shown in a first operable position, said needle trap having a releasable adhesive coated bandage ready to deploy and a mechanical lock joining the bandage to the needle guard.

FIG. 65 is a full side view of a covered hypodermic needle on a slidable needle guard of FIG. 64 showing the movable needle trap in a second position protective position covering the needle tip and the adhesive coated bandage released from the lock of the needle guard.

DETAILED DESCRIPTION

Figure 12:
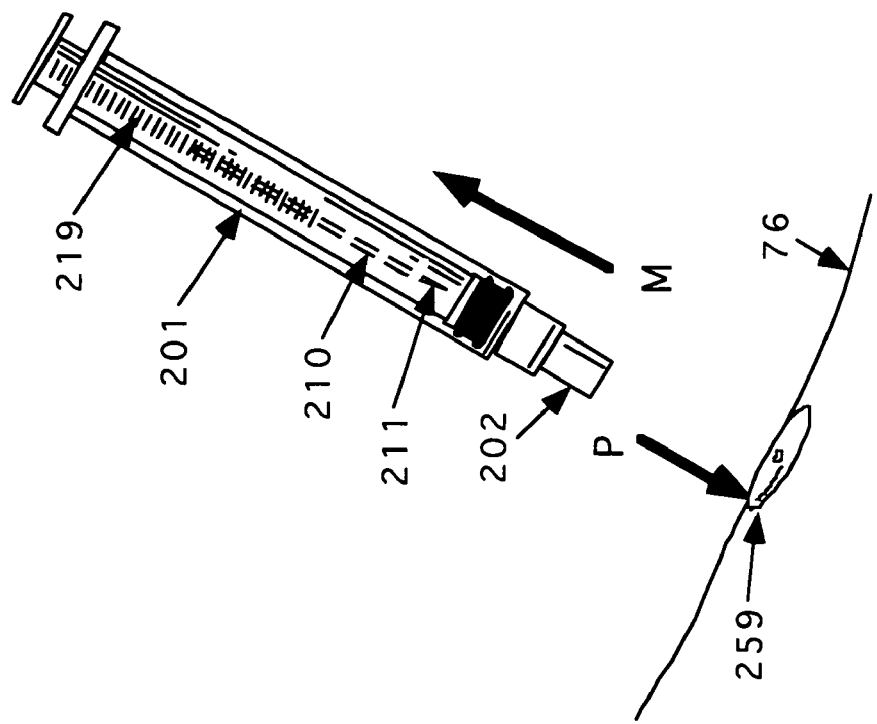
FIG. 12 is a full side view of the hypodermic apparatus of FIG. 11 showing a needle fully retracted into syringe body and the puncture site covered with a bandage or removable member that is released from syringe apparatus.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood however, that the same or equivalent functions and sequences may be accomplished by different embodiments and that they are also intended to be encompassed within the scope of the invention.

A means to indicate or cover the hypodermic puncture or wound site or a needle tip housing with a puncture site indicating or covering means is described. In the following description, numerous specific details are set forth in order to provide a thorough understanding of the present invention. However, it will be obvious to one of ordinary skill in the art that the invention may be practiced without these specific details. In other instances, well-known structures and processing steps have not been shown in particular detail in order to avoid unnecessarily obscuring the present invention. Additionally, it should be noted that throughout this discussion reference will be made to a variety of hypodermic needle devices such as fillable syringes, prefilled syringes, prefilled cartridge syringes, blood collection devices, percutaneous entry needles, implanted port needles and catheters. It is appreciated, however, that the present invention is not limited to these devices, and may be used in any application where it is desirable to provide a means to indicate or cover the puncture site, or a housing at the tip of a needle or other elongated object in combination with a means to indicate or cover the puncture or wound site. A method and apparatus to limit the penetration depth of a hypodermic needle is also disclosed.

It should also be understood that the various aspects of the present invention disclosed herein can easily be adapted to all types of procedures where a needle may be used, including, but not limited to, neurological, urological, central venous, oximetry, thermodilution, PTCA, PTA, angiography, atherectomy, electrophysiology, suction and wound drainage, cardiovascular, pulmonary and spinal catheters. The present invention described herein can also be easily adapted to a blood collection needle, or any other needles used in invasive procedures, including, but not limited to, angiography, cardiovascular, ophthalmologic, neurology, orthopedic, dentistry, veterinary, chemotherapy and arterial blood gas.

FIG. 1 is a full side view of a prior art injection method and apparatus with fluid being administered by syringe 1 having needle 10 with a sharpened distal tip 11 inserted in tissue 76. Needle 10 is shown in broken lines below the surface of the skin. Movement "M" of the plunger rod pushes fluid through needle 10 into tissue 76.

FIG. 2 is a full side view of the prior art injection method and apparatus of FIG. 1 with syringe 1 and needle 10 fully removed from the puncture site 95, movement indicated by bold arrow, and bandage 87 being placed on puncture site 95 of tissue 76.

FIG. 3 is a full side view of the prior art injection method and apparatus of FIGS. 1 and 2 with syringe 1 and the needle 10 fully removed from puncture site 95 and bandage 87 covering the puncture site of tissue 76.

FIG. 4 is a full side view of the injection method and apparatus of the present invention showing fluid being administered by syringe 101 having needle 110 with a sharpened distal tip 111 inserted in tissue 76. Syringe 101 and/or needle 110 includes a puncture site marker or indicator 102 at the proximal end of needle 110 that marks the puncture site during the procedure. Needle 110 is shown in broken lines below the surface of the skin. Movement "M" of the plunger rod pushes fluid through needle 110 into tissue 76. As will be appreciated by those skilled in the art, many diameters of hypodermic needles can be very small, and marking the puncture site during the procedure will assist the clinician in determining the exact location for applying a covering or bandage.

Any syringe disclosed herein may include an integrally "staked," or permanently bonded needle, a removable needle, a luer slip or luer lock fitting, may be fillable or prefilled, or include a self-destructive, one time use apparatus.

All the detachable members or bandages disclosed herein may include an adhesive coating, an absorbent material, and a selectively removable protective sheet covering the adhesive coating or absorbent material. The absorbent material may include or any type of medication that reduces infection probability, such as, but limited to, antibiotics, antimicrobials, vitamins, ointments or the like.

FIG. 5 is a full side view of the injection method and apparatus of FIG. 4 showing syringe 101 being withdrawn, movement indicated by bold arrow, from tissue 76 and puncture site 95 that is indicated by indicator 4, marking the exact location of puncture site 95. Mark 4 is deposited or dispensed by indicator 102 of syringe 101 and may comprise an ink, dye, pigment or colorant distinguishable from color of skin, and may include any ointment, antibiotic, antimicrobial, or the like to reduce infection probability.

FIG. 6 is a full side view of the passive injection method and apparatus of the present invention showing fluid being administered by syringe 101 and needle 10 inserted in tissue 76. Syringe 101 and/or needle 110 includes needle housing 22 having detachable member 59 at the proximal end of needle 110 that contacts and covers the puncture site during the procedure. Needle 110, having a change in profile 103 located on the needle shaft to limit axial movement of needle housing 22, is shown in broken lines below the surface of the skin. Said detachable member 59, is releasably coupled to said needle housing 22 by an adhesive, frictional, mechanical, separable, tearable or rotational means, and may include an adhesive and absorbent material. Said member 59 is releasably coupled to housing 22. Movement "M" of the plunger rod pushes fluid through needle 110 into tissue 76. A resilient member or spring may be included to urge a needle guard to the distal end of the needle in any of the embodiments disclosed herein.

FIG. 7 is a full side view of the injection method and apparatus of FIG. 6 showing syringe 101 being withdrawn, indicated by bold arrow, from the puncture site that is covered with a bandage or detachable member 59 that is releasably attached to needle housing 22. The fluid in syringe 101 has been administered to the patient or infusion port. Pressure "P" is shown being applied to at least one portion of the bandage 59 during needle 110 removal.

FIG. 8 is a full side view of the injection method and apparatus of FIGS. 6 and 7 showing syringe 101 fully withdrawn from the puncture site that is covered with a bandage or removable member 59 that is now released from needle housing 22. Pressure "P" is applied to bandage 59 after needle 110 removal. The distal needle tip is safely covered in housing 22.

FIG. 9 is a full side view of the passive injection method and apparatus of the present invention showing syringe 101 being withdrawn, indicated by bold arrow, from tissue 76 at the puncture site that is covered with a bandage or detachable member 159 that is releasably attached to needle housing 122. Axial movement of needle guard 122 is limited by tether 124. The fluid in syringe 101 has been administered to the patient or infusion port. Pressure "P" is shown being applied to at least one portion of bandage 159 during needle 110 removal. Said detachable member 159 having slit 89, is releasably coupled to said needle housing 122, and may include an adhesive and absorbent material.

FIG. 10 is a full side view of the injection method and apparatus of FIG. 9 showing syringe 101 fully withdrawn from tissue 76 that is covered with bandage or removable member 159 at the puncture site, said bandage 159 is now released from needle housing 122, with tether 124 limiting the axial movement of needle housing 22 along needle 110. Pressure "P" is applied to bandage 159 having slit 89, after needle 110 removal. The needle tip is safely covered in needle housing 122.

Figure 11:
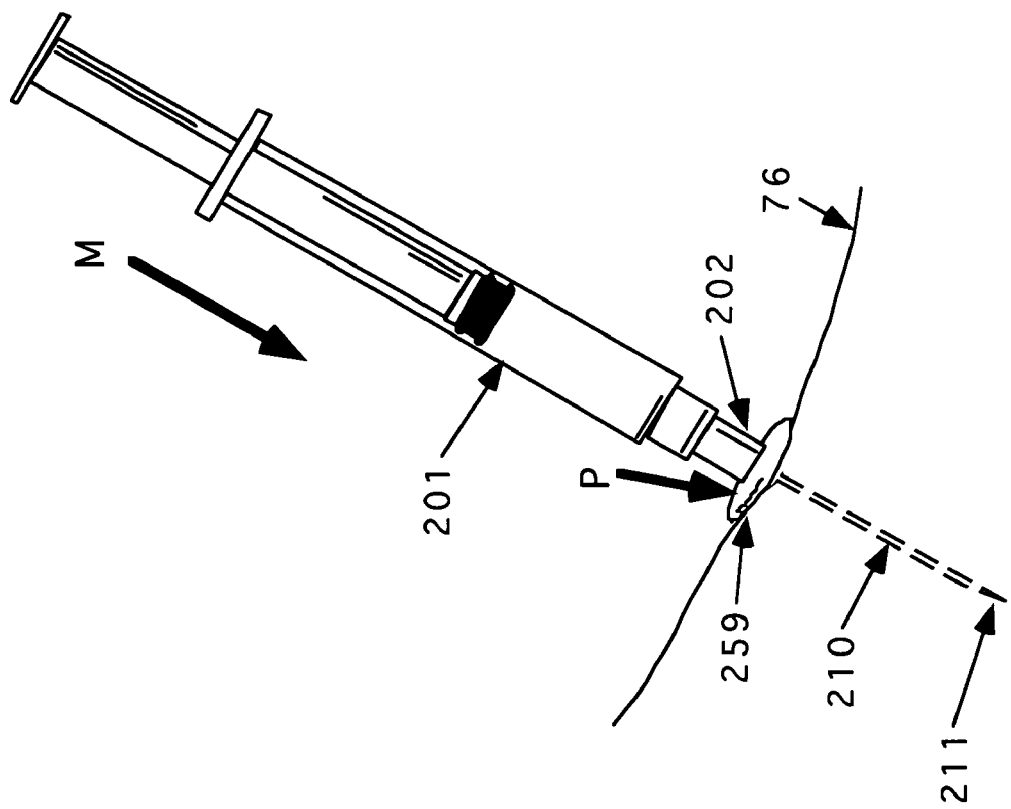
FIG. 11 is a full side view of the hypodermic apparatus of the present invention showing fluid being administered by a syringe with a retracting needle with said needle and sharpened tip inserted in tissue, and a puncture site cover contacting the surface of the skin.

FIG. 11 is a full side view of the injection method and apparatus of the present invention showing fluid being administered by syringe 201 with a retracting needle 210 with said needle 210 and sharpened tip 211 inserted in tissue 76. Syringe 201 and/or needle 210 includes a detachable member 259 at the proximal end of needle 210 that covers the puncture site during the procedure. The needle retraction mechanism can be activated by either further advancing the plunger after the medication is administered, or by securing the distal end 202 of syringe 201 and moving the body of the syringe 201 away from the distal end 202 of syringe 201 or puncture site, thus allowing needle 210 to retract into syringe 201 body. Needle 210 and tip 211 are shown in broken lines below the surface of the skin. Said detachable member 259 is releasably coupled to said distal end of syringe 202 or syringe 210, and may include an adhesive and absorbent material.

FIG. 12 is a full side view of the injection method and apparatus of FIG. 11 showing needle 210 fully retracted into syringe body 201 and the puncture site covered with a bandage or removable member 259 that is released from syringe apparatus 201. Pressure "P" is applied to bandage 259 after needle 210 retraction. Needle 210 and resilient member or spring 219 are shown in broken lines inside the syringe body 201. Needle 210 is safely inside syringe 201. Retraction means may include a vacuum, an elastomeric member or the like.

Figure 13:
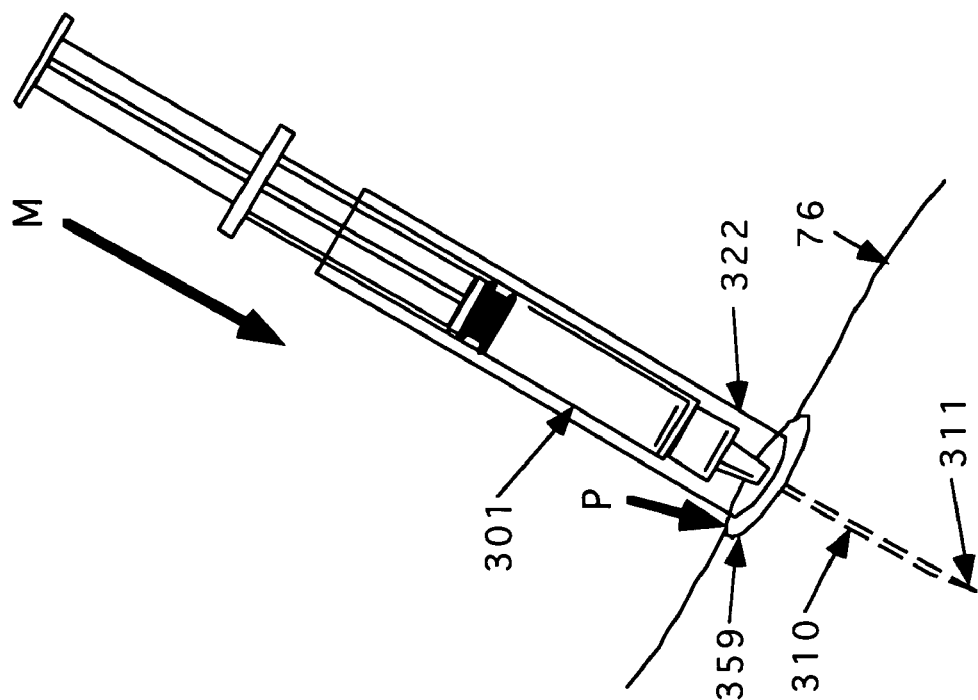
FIG. 13 is a full side view of the hypodermic apparatus of the present invention showing fluid being administered by a syringe having a movable sliding sleeve with the needle inserted in tissue. The sliding sleeve includes a detachable member at the distal end of the sleeve that covers the puncture site during the procedure.

FIG. 13 is a full side view of the injection method and apparatus of the present invention showing fluid being administered by syringe 301 having a movable sliding sleeve 322 with needle 310 inserted in tissue 76. Sliding sleeve 322 includes a detachable member 359 at the distal end of the sleeve 322 that covers the puncture site during the procedure. Needle 310 and tip 311 are shown in broken lines below the surface of the skin. Said detachable member 359, is releasably coupled to said sliding sleeve 322, and may include an adhesive and absorbent material.

Figure 14:
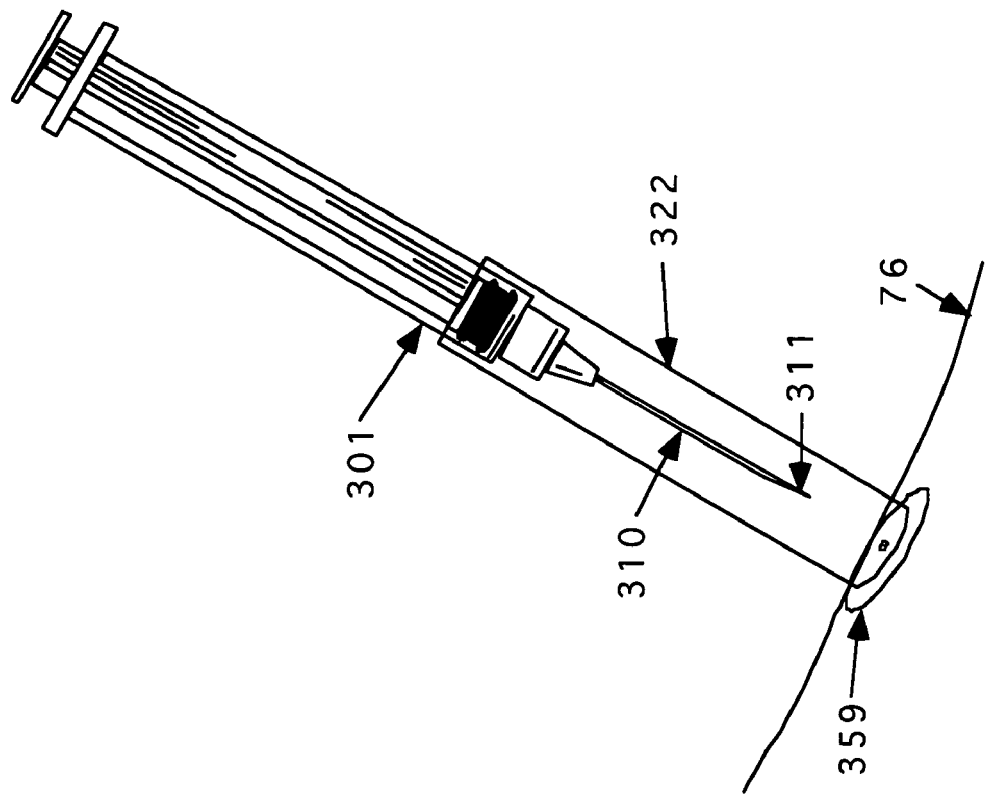
FIG. 14 is a full side view of the hypodermic apparatus of FIG. 13 showing the sliding sleeve fully deployed over the needle and the puncture site covered with a bandage or removable member that is releasable from the apparatus.

FIG. 14 is a full side view of the injection method and apparatus of FIG. 13 showing sliding sleeve 322 fully deployed over the needle 310 and the puncture site covered with bandage or removable member 359 that is releasably coupled to said sliding sleeve 322.

Figure 15:
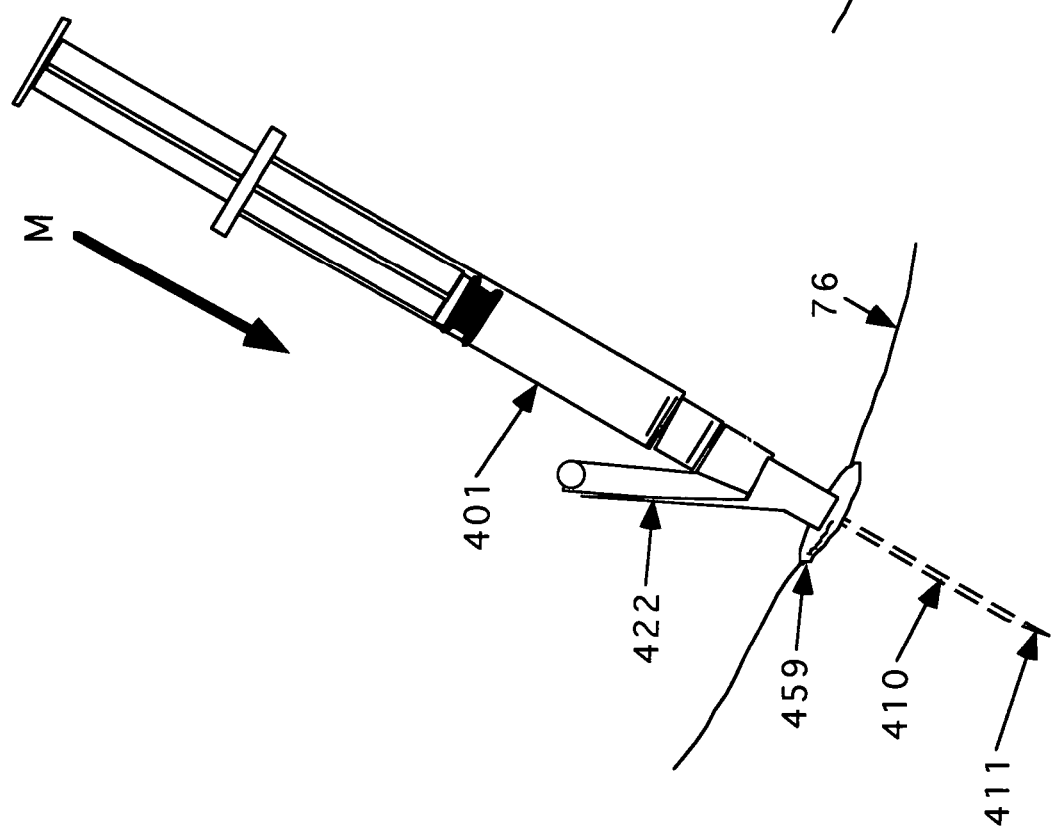
FIG. 15 is a full side view of the hypodermic apparatus of the present invention showing fluid being administered by a syringe having a needle with a movable sliding sleeve, with the needle inserted in tissue, and a puncture site cover contacting the surface of the skin.

FIG. 15 is a full side view of the injection method and apparatus of the present invention showing fluid being administered by syringe 401 having needle 410 with a distal sharpened tip 411, with a movable sliding sleeve 422, with needle 410 inserted in tissue 76. Sleeve 422 includes detachable member 459 at the distal end of sleeve 422 that covers the puncture site during the procedure. Needle 410 and tip 411 are shown in broken lines below the surface of the skin.

Figure 16:
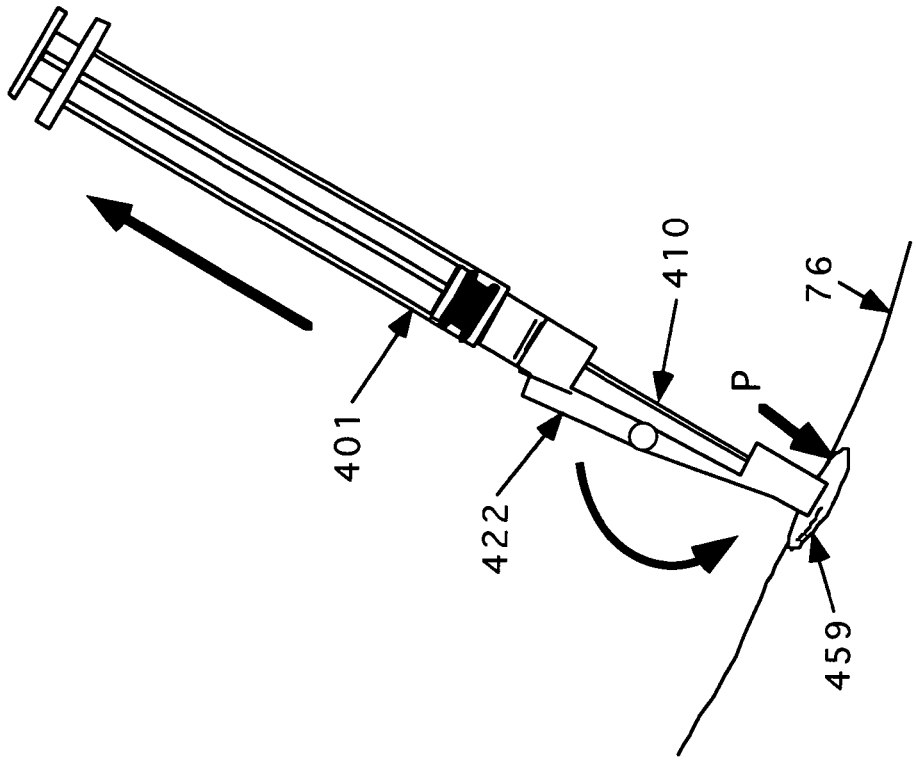
FIG. 16 is a full side view of the hypodermic apparatus of FIG. 15 showing the sliding needle guard fully deployed over the needle and the puncture site covered with a bandage or removable member that is released from the apparatus.

FIG. 16 is a full side view of the injection method and apparatus of FIG. 15 showing sliding sleeve 422 fully deployed over needle 410 and the puncture site covered with bandage or removable member 459 that is released from guard 422. Said detachable member 459, is releasably coupled to said sleeve 422, and may include an adhesive and absorbent material.

FIG. 17 is a full side view of the injection method and apparatus of the present invention showing fluid being administered by syringe 101 having needle 110 with a distal sharpened tip 111, with a puncture site cover 149 with needle 110 inserted in tissue 76. Syringe 101 or needle 110 includes detachable member 149 at the distal end of the apparatus that covers the puncture site during the procedure. Needle 110 and tip 111 are shown in broken lines below the surface of the skin. Detachable member 149 can be deployed or unfolded by a distal protrusion 141 or proximal protrusion 142. A protective sheet 140 is removable from detachable member 149 by a distal protrusion 141, or protective sheet 143 is removable from detachable member 149 by a proximal protrusion 142. Said detachable member 149, is releasably coupled to said needle 110 or syringe 101, and may include an adhesive and absorbent material.

FIG. 18 is a full side view of the injection method and apparatus of FIG. 17 showing needle 110 fully removed from the puncture site and detachable member or bandage 149 ready to be attached to the surface adjacent to the puncture site. Bandage 149 may include a distal protrusion 141 or proximal protrusion 142.

FIG. 19 is a cross sectional side view of a hypodermic apparatus of the present invention that includes a puncture site indicator comprising needle 10 attached to hub 14, said needle 10 having a sharpened distal tip 11, and a means 29 to mark or indicate a puncture site. Puncture site indicator 29 comprises a material that deposits a dye, coloring, pigment or the like on the tissue or surface at the puncture site when the entire length of needle 10 is inserted into tissue and distal end of hub 14 contacts the tissue or a separate surface during the procedure. Puncture site indicator 29 may be an integral, or a removable part of hub 14.

FIG. 20 is a cross sectional side view of a hypodermic apparatus of the present invention that includes a movable puncture site indicator comprising puncture site indicator 129 on needle 10 having a sharpened distal tip 11 and hub 14 at proximal end of needle 10, said movable puncture site marker 129 having an aperture 47 therethrough. Puncture site indicator 129 is releasably retained adjacent to the proximal end of needle 10 and engages skin or tissue when entire length of needle 10 is inserted into tissue. Removable puncture site indicator 129 may comprise a material that disperses or deposits a dye, coloring, an anesthetic, antimicrobial or other medication at the puncture site when the entire length of the needle 10 is inserted into tissue and the puncture site indicator 129 engages surface or tissue. An adhesive, mechanical, frictional, breakable or rotational means may also retain puncture site indicator 129 adjacent to needle hub 14 prior to the insertion procedure. An adhesive may also selectively attach puncture site indicator 129 to tissue during the insertion procedure. Puncture site indicator 129 may be manually slid along axis of needle 10 during procedures where the entire length of needle 10 is not inserted into tissue.

FIG. 21 is a cross sectional side view of the removable puncture site indicator of FIG. 20 showing puncture site indicator 129 having an aperture 47, separated from needle 10 having a sharpened distal tip 11 and hub 14 at proximal end of needle 10. Puncture site indicator 129 may include an adhesive to selectively attach puncture site indicator 129 to tissue during or after the insertion procedure.

FIG. 22. is a full front view of the removable puncture site indicator of FIGS. 20 and 21 along axis 22-22 comprising a slidable puncture site indicator 129 having an aperture 47 with a needle 10 therethrough.

FIG. 23 is a cut away side view of slidable puncture site indicator 229 of the present invention on a cross sectional view of needle 10 having a sharpened distal tip 11, slidable puncture site indicator 229 being releasable retained adjacent slidable member 222 by an adhesive, formed, mechanical, frictional, separable, tearable or rotational means. Slidable puncture site indicator 229 having an aperture 247 allowing puncture site indicator 229 and member 222 to be placed, and slide axially on, needle 10. Slidable member 222 may incorporate any of the features of any needle guard embodiments disclosed in the specification and drawings of this document.

FIG. 24 a cut away side view of slidable puncture site indicator of FIG. 23 shown on a cross sectional view of needle 10 having a sharpened distal tip 11, slidable puncture site indicator 229 being moved to the distal end of needle 10 for marking a puncture site.

FIG. 25 is a full front view of the puncture site indicator of FIG. 23 in axis 25-25 comprising a needle 10 through aperture 247 of slidable puncture site indicator 229 being releasably attached to slidable member 222.

FIG. 26 is a full top view of a bandage of the present invention for covering a puncture site comprising a puncture site cover 329 that may include an adhesive coating for attachment to tissue, an absorbent member 187 or portion, shown in broken lines on the underside of said bandage 329, and a slit 189. Slit 189 makes it possible to side load puncture site cover 329 onto a needle apparatus or needle. Slit 189 may include portions that overlap and adhere to each other. Absorbent portion 187 of puncture site cover 329 may include an anesthetic, antimicrobial or other medication. Any puncture site cover embodiments shown in this document may include a means or aperture for mechanically retaining a puncture site indicator or cover to any needle guard disclosed herein.

FIG. 26 is a full top view of a different embodiment of the puncture site cover of the present invention for covering a puncture site comprising a puncture site covering 429 having an adhesive coating for attaching to tissue, an absorbent member or portion 287, shown in broken lines on the underside of said bandage 329, and a slit or aperture 289. Slit or aperture 289 allows bandage 429 to accommodate needle 10. Slit 289 may include portions that overlap and adhere to each other. Absorbent or dispensing portion 287 of puncture site cover 259 may include an anesthetic, antimicrobial or other medication.

FIG. 28 is a full top view of a puncture site indicator or cover of the present invention showing puncture site cover or indicator 529 having an aperture 347 and tab or protrusion 321. Tab 321 may be used to attach puncture site cover 529 to tissue. Tab 321 may also be folded over and used to cover aperture 347 of puncture site cover 529.

FIG. 29 is a full side view of a simple, one-piece needle housing or member 22 on needle 110 having a sharpened distal tip 111 and change in profile 103 which may be utilized to deploy the site indicator or puncture site covers of the present invention. Needle housing 22 includes an inner chamber or cavity 431 for engaging change in profile 1033 of needle 110 there within.

FIG. 30 is a full side view of the one-piece needle housing of FIG. 29 showing housing 22 locked on the distal end of needle 110. Change in profile 103 of needle 110 is also confined within the housing 22. In this regard, housing 22 is axially moved along needle 110 where inner chamber 431 of housing 22 binds, engages, impacts, locks or interferes with change in profile 103 of needle 110. Housing 22 includes an aperture 447 allowing such housing 22 to slide on needle As will be appreciated, housing 22 may also comprise a plurality of corresponding sections that create a similar configuration when joined together.

FIG. 31 is a cut away front view of the housing of FIGS. 29 and 30 along axis 31-31 comprising a member 22, an aperture 447 and an inner chamber or cavity 431.

FIG. 32 is a cross-sectional side view of an alternative embodiment of the housing of the present invention with sliding member 123, shown in a side cut away view, locked or bound at the distal end of the needle 110. Said apparatus has a needle 110 with sliding member 123 with an aperture therethrough comprising a proximal section 124, an enlarged intermediate section 131, an intermediate section 125 sized similarly to said proximal section 124, and an enlarged distal section 126 that provides a "relief" section that does not engage needle 110 or change in profile 103 as guard 123 is moved toward the distal end of needle 110. Said needle 110 having a change in profile 103 on the needle 110 shaft to limit axial movement of said sliding member 123. When said member 123 is slid toward the distal end of needle 110, distal section 126 of said member 123 is larger than change in profile 103 of needle 110 and said distal section 126 does not contact said change in profile 103, allowing initial contact or interference to be made by intermediate section 125. Axial movement of slidable member 123 is limited by engagement of said change in profile 103 in enlarged intermediate section 131 of said member 123. Proximal aperture or shaft 124 includes a diameter approximately equal to diameter of intermediate section 125. Change in profile 103 of the needle 110 shaft and distal needle tip 111 are confined within said sliding member 123.

FIG. 33 is a cross-sectional side view of another embodiment of the present invention with sliding member or needle guard 223 located on said needle 110 shaft, said needle 110 having change in profile 103 to limit axial movement of said sliding member 223, wherein said sliding member 223 is capable of going off axis to trap needle tip 111 in guard 223 when distal protrusion 227 moves in front of distal needle tip 111. Sliding member 223 has a larger proximal aperture or opening 234 and distal aperture or opening 226 relative to inner sections 231, 224 and 225, and a protrusion 227 on the distal end sliding member 223. Change in profile 103 lodges or binds in inner section 231 to stop axial movement of said needle guard 223 on needle 110. When member 223 is slid toward the distal end of needle 110, distal section 226 of said member 223 is larger than change in profile 103 of needle 110 and said distal section 226 does not contact said change in profile 103, allowing initial contact or interference to be made by intermediate section 225. Axial movement of slidable member 123 is limited by engagement of said change in profile 103 in enlarged intermediate section 231 of said member 223.

FIG. 34 is a cross-sectional side view of FIG. 33 with the sliding member 223 locked at the distal end of the needle 110, said sliding member 223 capable of going off axis to trap needle tip 111 in guard 223 when distal protrusion 227 moves in front of distal needle tip 111. Said needle 110 having a change in profile 103 intermediate on the needle shaft to limit axial movement of said sliding member 223. Said distal needle tip 111 now being contained within distal portion of said sliding member 223 and positioned behind said protrusion 227 on the distal end of said larger aperture 226.

FIG. 35 illustrates a needle of the present invention comprising a needle 110 having an elongated change in profile 203, that includes a proximal portion 204 and a distal portion 205, near the sharpened needle tip 111 with a sliding bushing or washer 130 on the needle 110. Change in profile 203 of needle 10 may comprise at least one elongated portion, and may comprise a plurality of deformations 204 and 205. Along these lines, change in profile 203 of needle 110 may comprise a plurality of deformations 204 and 205 that create recess 203 on needle 110. In this regard, sliding member 130 may axially slide past first proximal deformation 204 and lock between said proximal deformation 204 and distal deformation 205 in recess 203 on needle 110.

FIG. 36 is a full side view of needle 110 and a cut away view of a needle housing or sliding member 1022 of the present invention illustrating a needle 110 having a plurality of changes in profile 203, 204 and 205 near the sharpened needle tip 111 with sliding member 1022 located on said needle 110. Said sliding member 1022 having a plurality of inner chambers or cavities 231, 232 and 233 for engaging changes in profile 203, 204 or 205 of said needle 110. Said inner chamber 232 may also individually engage change in profile 204.

FIG. 37 is a cross-sectional side view of the needle of FIG. 36 with the sliding member 1022 locked at the distal end of the needle 110, said member 1022 covering sharpened needle tip 111. The changes in profile 203, 204 and 205 of needle 110 are confined within inner chambers or cavities 231, 232 and 233 of said sliding member 1022 that is shown in a cut away side view. Change in profile 213 may comprise a thicker wall section of additional material.

Figure 38:
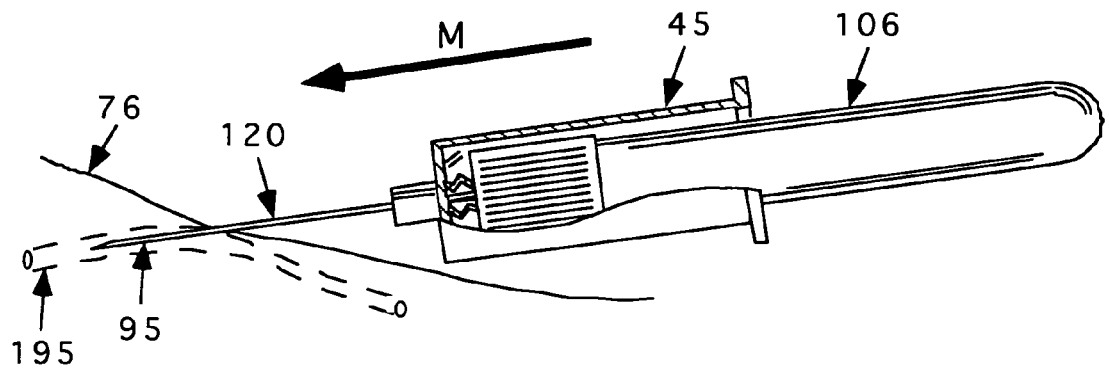
FIG. 38 is a full side view of a prior art blood or fluid collection method and apparatus with fluid being removed by a vacuum tube that is punctured by the proximal end of a double ended needle, with the distal end of said needle inserted in a blood vessel.

FIG. 38 is a full side view of a prior art fluid collection method and apparatus with fluid being removed by a vacuum tube 106 that is punctured by the proximal end of a double ended needle 120 that is inserted in blood vessel 195 of tissue 76 at puncture site 95. Needle 120 is removably held in needle holder 45. Blood vessel 195 is shown in broken lines below the surface of the skin. Multiple samples can be taken with a single needle 120 by inserting a variety of blood collection tubes 106 into the needle holder 45. As is well-known, risk of injury to the clinician is very high after needle withdrawal if they are stuck with the contaminated needle that is now filled with the patient's blood.

Figure 39:
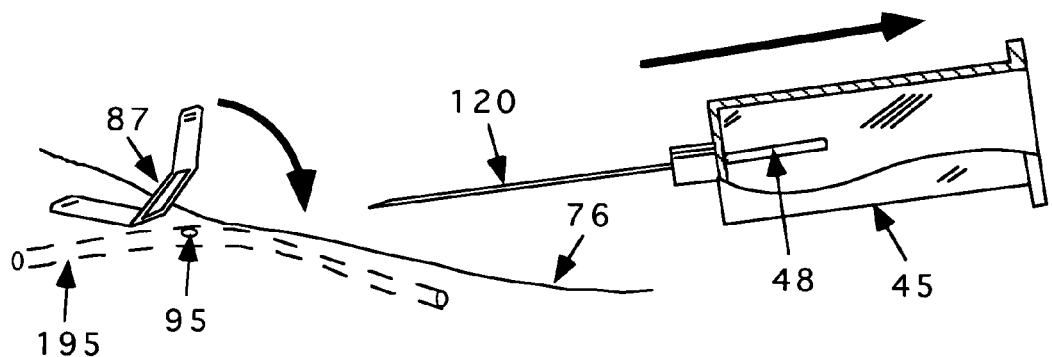
FIG. 39 is a full side view of a prior art fluid collection method and apparatus of FIG. 38 with the exposed needle removed from the tissue and a bandage being placed on the puncture site.

FIG. 39 is a full side view of the inferior prior art fluid collection method and apparatus of FIG. 38 with the contaminated, exposed needle 120 fully removed from blood vessel 195 of tissue 76 and bandage 87 being placed on puncture site 95. Blood vessel 195 is shown in broken lines below the surface of the skin. Needle 120 is removably held in needle holder 45. Pressure is applied to a cotton ball that is often placed over puncture site 95 before needle 120 is removed from puncture site 95 to absorb any fluid that leaks from puncture site 95 after needle 110 is removed from blood vessel 195. A bandage 87 is then placed over cotton ball to secure it to the skin.

Figure 40:
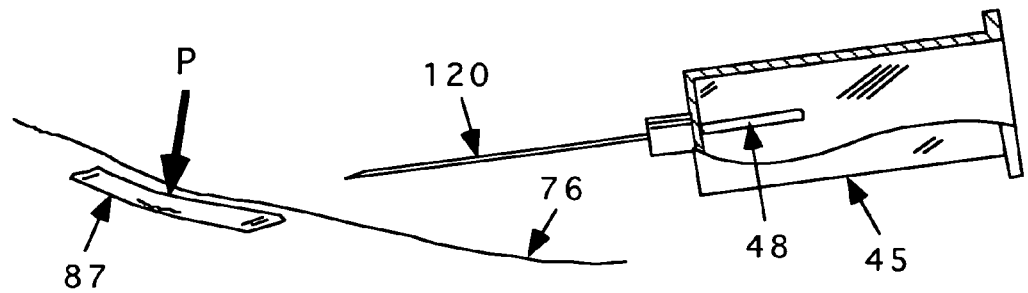
FIG. 40 is a full side view of a prior art fluid collection method and apparatus of FIGS. 38 and 39 with the exposed needle fully removed from the puncture site, and a bandage covering the puncture site.

FIG. 40 is a full side view of the interior prior art fluid collection method and apparatus of FIG. 38 and 39 with the contaminated, exposed needle 120 fully removed from tissue 76 and bandage 87 fully placed over puncture site 95. Needle 120 is removably held in needle holder 45. Continued pressure is applied to bandage 87 securing it to the skin.

FIG. 41 is a full side view of the passive fluid collection method and apparatus of the present invention showing fluid being collected with a safety hypodermic apparatus that includes a needle guard 522 with a deployable puncture site cover 589. The fluid is removed by vacuum tube 106 that is punctured by the proximal end, covered by boot 548, of double ended needle 510 that is inserted through tissue 76 at puncture site 95 and into a blood vessel 195. Blood vessel 195 is shown in broken lines below the surface of the skin. Slidable member 522 is shown in a full side view on needle 510, adjacent to needle holder 504, shown in a cut away view. Puncture site cover 559 is releasably attached to slidable member 522 by adhesive, frictional or mechanical means or the like. Puncture site cover 559 may include an absorbent portion 588, an adhesive portion for attaching bandage 559 to tissue and may include a tab 521 to assist in deploying bandage 559 over puncture site 95. The bold straight arrow indicates movement of the needle apparatus into the blood vessel.

The multitude of hypodermic needle apparatus shown herein disclose puncture site indicators or covers 29, 59, 102, 129, 149, 159, 229, 259, 359, 459 all being deployable along the axis of the needle and may include an aperture suitable to surround a needle 10, 110, 210, 310, 410. The multitude of hypodermic needle apparatus shown herein disclose puncture site indicators or covers 559, 659, 859, 959 and 1059 all being deployable from a side of a needle 510, 610, 810, 910 and 1110. An aperture may be included on a portion of the puncture site cover for releasably attaching the puncture site cover to a hypodermic needle or apparatus. Although the puncture site cover 559 is shown folded twice in this embodiment, it is noted that a variety of folds may be used to store and deploy the puncture site cover. The puncture site covers disclosed herein may also include a puncture proof material or armor to reduce needle penetration probability. At least one fold may be used to retain puncture site cover adjacent to, or within, a needle guard or hypodermic apparatus. The puncture site cover may be deployed by a sliding, unrolling, unfolding or other extending or deployable means.

FIG. 42 is a full side view of the fluid collection method and apparatus of FIG. 41 showing needle guard 522 with puncture site cover 559 being deployed over puncture site 95 with needle 510 still in blood vessel 195. Needle holder 504, shown in a cut away view, holds needle 510 now remaining in blood vessel 195 at puncture site 95. Vacuum tube 106 has now been removed from needle holder 504 with boot 548 covering proximal end of needle 510 where distal end of needle 510 remains in blood vessel 195 at puncture site 95. Boot 548 on needle 510 keeps blood in needle 510 from leaking into needle holder 504. Blood vessel 195 is shown in broken lines below the surface of the skin 76. Slidable member 522 is shown in a full side view on needle 510, adjacent to needle holder 504. A curved arrow shows puncture site cover 559 being unfolded or deployed from the side of slidable member 522. Puncture site cover 559 is releasably attached to member 522 by an adhesive, frictional or mechanical means or the like. Puncture site cover 559 includes an absorbent portion 587, an adhesive portion for attaching bandage 559 to tissue and may include a tab 521 to assist in deploying bandage 559 over puncture site 95.

Figure 43:
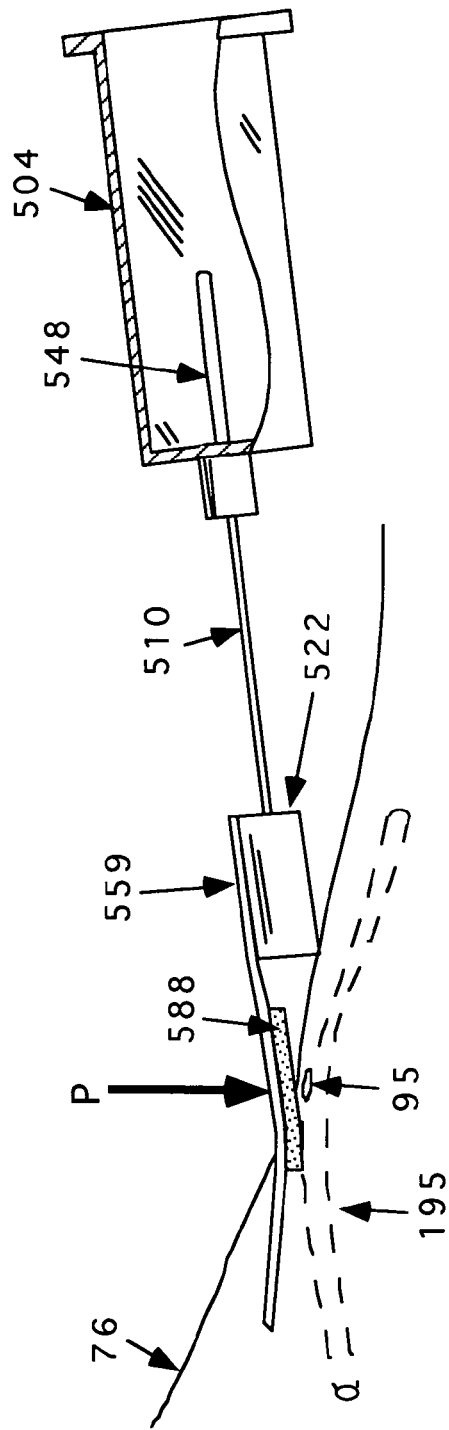
FIG. 43 is a full side view of the fluid collection method and apparatus of FIGS. 41 and 42 showing the distal end of a bandage extended over and covering a puncture site, with a bandage releasably coupled to the slidable member.

FIG. 43 is a full side view of the fluid collection method and apparatus of FIGS. 41 and 42 showing a needle 510 safely trapped within slidable member 522 with puncture site 95 cover safely deployed over puncture site 95 with needle 510 fully removed from blood vessel 195. Blood vessel 195 is shown in broken lines below the surface of the skin 76. Slidable member 522 is shown in a full side view on needle 510, adjacent to needle holder 504. A straight arrow "P" indicates manual pressure being placed near or on puncture site 95 and shows puncture site cover 559 fully unfolded and releasably attached to slidable member 522. Puncture site cover 559 is releasably attached to needle guard 522 by an adhesive, frictional or mechanical means or the like. Puncture site cover 559 includes an absorbent portion 587 now covering puncture site 95, and an adhesive portion for attaching bandage 559 to tissue 76. Puncture site cover 559 is fully deployed over puncture site 95 and needle 510 is safely removed from blood vessel 195 and puncture site 95.

Figure 44:
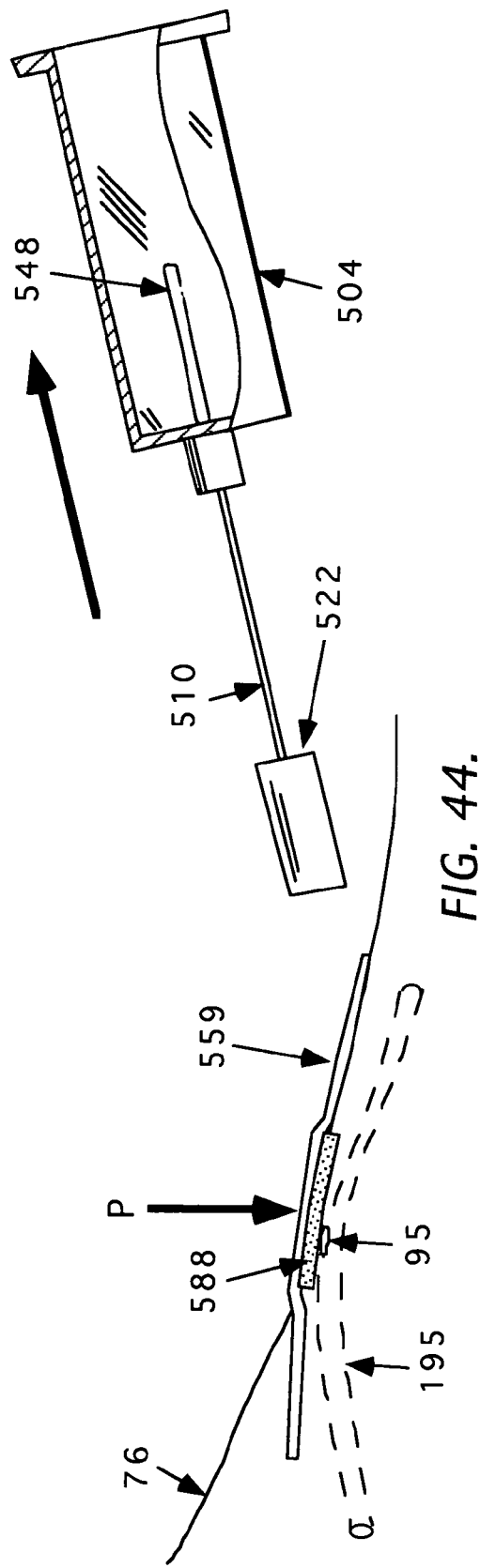
FIG. 44 is a full side view of the fluid collection method and apparatus of FIGS. 41-43 showing a bandage covering the puncture site and fully disengaged from the slidable member.

FIG. 44 is a full side view of the fluid collection method and apparatus of FIGS. 41-43 showing needle 510 safely trapped within needle guard 522 with disengaged puncture site cover 559 safely covering puncture site 95 after needle 510 is fully removed from blood vessel 195. Needle holder 504 holds covered needle 510 now safely removed from blood vessel 195 and puncture site 95. Blood vessel 195 is shown in broken lines below the surface of skin 76. Slidable member 522 is shown in a full side view axially extending about needle 510, adjacent to needle holder 504. A straight arrow "P" indicates manual pressure being placed on puncture site 95 and shows puncture site cover 559 fully unfolded, deployed and separated from slidable member 522. Puncture site cover 559 is releasably attached to member 522 by an adhesive, frictional or mechanical means or the like. Puncture site cover 559 includes an absorbent portion 587 now covering puncture site 95, and an adhesive portion for attaching bandage 559 to tissue 76.

Figure 45:
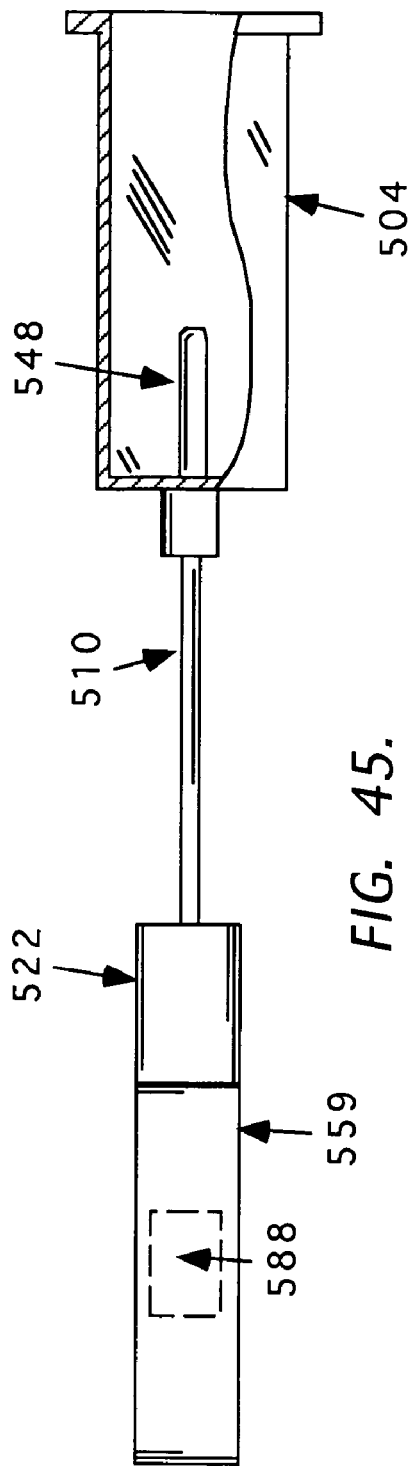
FIG. 45 is a full top view of the blood or fluid collection method and apparatus of FIGS. 41-44 showing a member or bandage deployed on the same axis as the needle.

FIG. 45 is a full top view of the blood or fluid collection method and apparatus of FIGS. 41-44 showing a member or bandage 559 deployed on the same axis as the needle 510. Said cover 559 may include and adhesive coating and an absorbent material 588.

Figure 46:
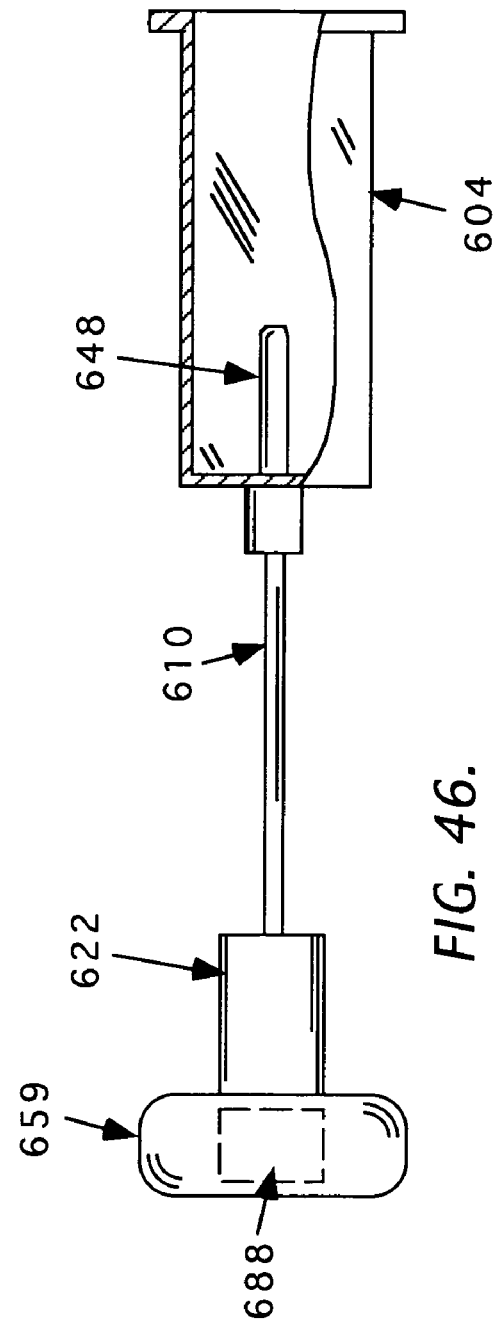
FIG. 46 is a full top view of the blood or fluid collection method and apparatus of the present invention showing a member or bandage deployed on a different axis relative to the axis of the needle.

FIG. 46 is a full top view of the blood or fluid collection method and apparatus of the present invention showing a member or bandage 659 deployed on a different axis relative to the axis of the needle 610. Said deployable member 659 is releasably coupled to said needle guard 622, and may include an adhesive coating and absorbent material 688.

FIG. 47 is a full top view of a prior art winged infusion or "butterfly" needle apparatus comprising needle 710 with sharpened distal end 711, having a proximal end attached to hub 715, and a plurality of flexible protrusions or wings 716 and 717 on said hub body 715 and a flexible tube 713 being attachable, usually by a luer fitting, to an infusion line or blood collection tube holder.

FIG. 48 is a full frontal view of a prior art winged infusion or "butterfly" needle apparatus shown in FIG. 47 having a hub body 715 with the plurality of flexible protrusions or wings 716 and 717 being bent or folded approximately 90° relative to needle 710 axis. Said wings 716 and 717 are usually gripped in this manner by the user to aid in the insertion of needle 710 into tissue.

FIG. 49 is a full top view of a passive winged infusion or "butterfly" needle apparatus of the present invention comprising a needle 810 with a sharpened distal end 811, having a proximal end attached to hub 815, and a plurality of flexible protrusions or wings 816 and 817 on said hub body 815 and a trailing tube 813 being attachable, usually by a luer fitting, to an infusion line or blood collection tube holder. A deployable member 859 is shown being unfoldable from a first position, and releasably coupled to said flexible wings 816 and 817, and may include an adhesive and absorbent material 888 shown on the top surface of member 859. Needle tip 811 is inserted into a blood vessel and fluid is infused into the patient, or a blood sample may be obtained when the trailing end 813 is connected to a vacuum tube or syringe.

FIG. 50 is a full top view of a winged infusion or "butterfly" needle apparatus of FIG. 49 with the deployable member or bandage 859 now folded or moved to a second position covering the puncture site, yet still releasably coupled to wings or protrusions 816 and 817. Needle 810 is shown in full view, but is actually still inserted blood vessel. Absorbent material 888 is shown on underside of bandage in broken lines. Pressure is placed on bandage 859 to anchor or stabilize said bandage 859 at puncture site.

FIG. 51 is a full top view of a winged infusion or "butterfly" needle apparatus of FIGS. 49 and 50 with the deployable member or bandage 859 covering puncture site and needle 810 and hub 815 being moved axially away from said puncture site and said bandage 859 that is releasably coupled to winged section 816 and 817. Pressure is maintained on said deployable member 859 or wings 816 or 817, anchoring bandage/wings at said puncture site. A means for securing winged section 816 and 817 to distal end of needle 810 may include a binding or gripping means, a limiting means such as a tether attached to said hub, or a change in profile that engages a slidable needle guard as disclosed in other embodiments in this application.

FIG. 52 is a full top view of a winged infusion or "butterfly" needle apparatus of FIGS. 49-51 with the deployable member or bandage 859 safely covering the puncture site, now safely separated from said needle apparatus. Pressure is maintained on said bandage 859 at said puncture site to stop bleeding. The needle tip 811 is contained within wings 816 and 817.

FIG. 53 is a full frontal view of the passive winged infusion or "butterfly" needle apparatus of FIGS. 49-52 having hub body 815 and a plurality of flexible protrusions or wings 816 and 817 being bent or folded approximately 90° relative to needle 810 axis. Said wings 816 and 817 are usually gripped in this manner by the user to aid in the insertion of the needle 810 into tissue. A deployable member 859 is releasably coupled to said wings 816 and 817.

FIG. 54 is a full top view of another embodiment of the passive winged infusion or "butterfly" needle apparatus of the present invention comprising a needle 910 with a sharpened distal end 911, having a proximal end attached to hub 915, and a plurality of flexible protrusions or wings 916 and 917, a sliding sleeve hub body 914 and trailing tube 913 being attachable, usually by a luer fitting, to an infusion line or blood collection tube holder. Deployable member 959 is shown in a first position and releasably coupled to said sliding sleeve 914, and may include an adhesive and absorbent material 988.

FIG. 55 is a full frontal view of the passive winged infusion or "butterfly" needle apparatus of FIG. 54 having plurality of flexible protrusions or wings 916 and 917 on hub body 915 being bent or folded approximately 90° relative to needle 910 axis. Said wings 916 and 917 are usually gripped in this manner by the user to aid in the insertion of the needle into tissue. Deployable member 959 is releasably coupled to said sliding sleeve hub body 914.

FIG. 56 is a full top view of a winged infusion or "butterfly" needle apparatus of FIGS. 54 and 55 with the deployable member or bandage 959 now unfolded or moved to a second position covering the puncture site, yet still releasably coupled to sliding sleeve hub body 914. Deployable member 959 is shown covering puncture site. Absorbent material 988 is shown on underside of bandage in broken lines. Pressure "P" anchors bandage 959 at puncture site while hub 915 is moved "M" away from said bandage 959 and sliding sleeve 914.

FIG. 57 is a full top view of a winged infusion or "butterfly" needle apparatus of FIGS. 54-56 with the deployable member or bandage 959 covering the puncture site, now safely separated from said sliding sleeve apparatus 914. Pressure is maintained on said bandage 959 at said puncture site to stop bleeding. The needle tip is now safely contained within said sliding sleeve needle guard 914.

FIG. 58 is a full top view of another embodiment of the winged infusion or "butterfly" needle apparatus of the present invention having a slidable deployable member or bandage 1059 now moved to a second position covering the puncture site, yet still releasably coupled to sliding sleeve hub body 1014. Deployable member 1059 is shown covering puncture site. Absorbent material 1088 is shown, attached and stored on underside of bandage 1059 in broken lines. Pressure "P" anchors bandage 1059 at puncture site while hub 1015 is moved "M" away from said bandage 1059 and sliding sleeve 1014.

FIG. 59 is a full top view of a winged infusion or "butterfly" needle apparatus of FIG. 58 with slidable, deployable member or bandage 1059 covering the puncture site, now safely separated from sliding sleeve apparatus 1014. The needle tip is now safely contained within said sliding sleeve needle apparatus 1014. Pressure "P" anchors bandage 1059 at puncture site to stop bleeding while hub 1015 is moved "M" away from said bandage 1059 and sliding sleeve 1014.

FIG. 60 is a cross sectional side view of a prior art hypodermic syringe 101 and needle 10 being inserted into vial 41 through stopper 40 to draw fluid 42 into said syringe 101. A lubricating film is applied to all hypodermic needles to minimize tissue drag during insertion into tissue.

FIG. 61 is a cross sectional side view of a hypodermic needle 1110 of the present invention comprising a needle 1110 coated with a lubricating film such as silicone 1112, a sharpened distal tip 1111 and a visual depth indicator 1103. Visual depth indicator 1103 may be comprised of any type of change in structure optically visible with or without magnification, or an added mark, that allows user to gauge depth of penetration of needle 1110 into a stopper or tissue.

FIG. 62 is a cross sectional side view of the hypodermic needle of FIG. 61 showing the needle 1110 being inserted partially through a stopper 40 of vial 41 to access fluid 42 contained within said vial 41. If needle 1110 is only partially inserted through stopper 40, then lubricating film or coating 1112 remains intact to reduce tissue drag when said needle 1110 is inserted into tissue.

FIG. 63 is a full bottom view of bandage 1259 of the present invention having an adhesive coated surface 1258, an absorbent member or area 1288 and aperture 1232 for releasably attaching said bandage 1259 to needle guard 1222.

FIG. 64 is a full side view of the present invention showing an exposed, ready to use hypodermic needle 1210 having a change in profile or enlargement 1203 on the shaft proximal to the sharpened distal tip 1211 and, and a partial cutaway view of slidable needle guard 1222 having movable needle trap 1241 shown in a first operable position, said needle trap 1241 having a protrusion 1242 for retaining aperture 1232 of member or adhesive coated bandage 1259 in a first operative position, said bandage 1259 having an aperture 1232, and absorbent member 1288, extended tab 1221 for gripping, and an adhesive coating 1258. Needle guard 1222 formed having top 1223 with an axial slot formed by the manufacture of said needle guard 1241 and a front top member 1219, bottom 1255, rear 1218 having an aperture for accepting a hypodermic needle 1210 and hinge 1240 connecting movable needle trap 1241 to needle guard 1222, and a front base side 1217 for joining to said front top member 1219 to form needle guard 1222.

FIG. 65 is a full side view the needle protective apparatus 1222 of FIG. 64 showing a covered and trapped hypodermic needle tip 1211 of hypodermic needle 1210 having a change in profile or enlargement 1203 engaging rear member 1218 of needle guard 1222 limiting axial movement of said guard 1222 and bandage 1259 with absorbent member 1288 positioned over puncture site, said bandage 1259 now extended away from and distal of said guard 1222 with movable needle trap 1241 with protrusion 1242 shown in a second released or retracted position, said protrusion 1242 having released hold on bandage 1259 via insertion through aperture 1232 of bandage 1259. Said needle trap 1241 having a proximal hinge 1240 connected to said rear member 1218, and plurality of skirts 1249 and 1245 for creating a containment area or chamber with said guard 1222. Front base member 1217 and front top member 1219 are joined together by inserting protrusion or coupler 1229 through aperture 1228.

Figure 66:
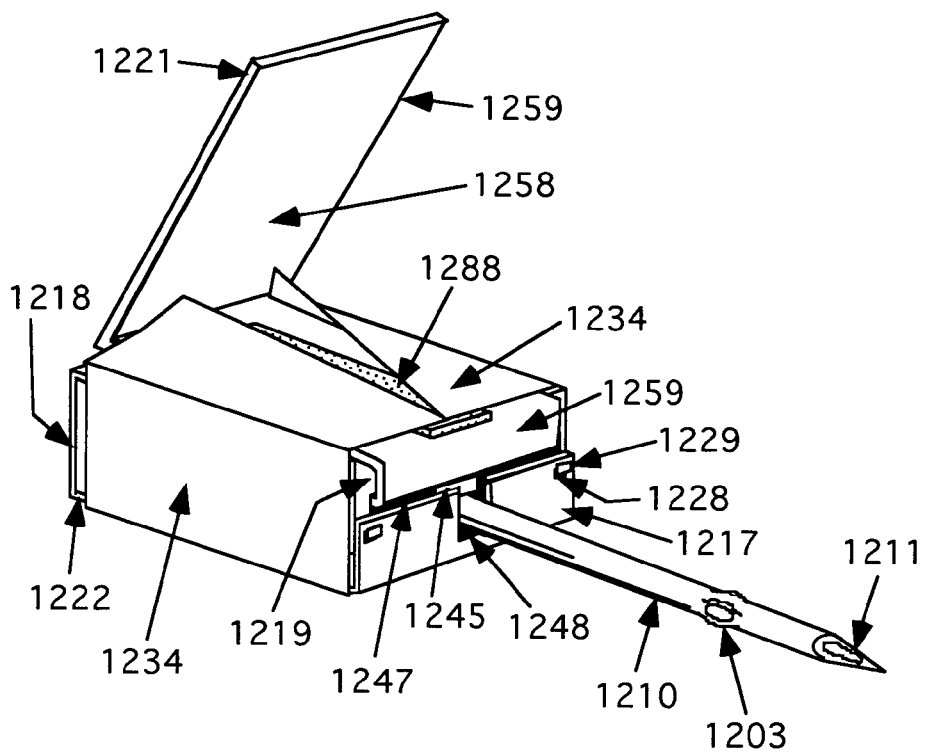
FIG. 66 is a full isometric view of a needle protective apparatus of the present invention showing an exposed hypodermic needle having a needle guard with an adhesive coated bandage being initially deployed from the needle guard and the release liner automatically being separated from the adhesive face or faces of the bandage.

FIG. 66 is a full isometric view of a needle protective apparatus 1222 of the present invention showing a partially deployed puncture site cover or bandage 1259 and uncovered hypodermic needle 1210 having a sharpened distal tip 1211 and enlargement 1203 to limit axial movement of guard 1222 on said needle 1210. Bandage 1259 having an absorbent member 1288 for covering a puncture site and adhesive film or coating 1258 for securing about a puncture site. A releasable liner 1234 surrounds said needle guard 1222 and maintains sterility of absorbent member 1288 during storage before use. As extended end 1221 of bandage 1259 is moved away from guard 1222, releasable liner 1234 remains attached to said guard 1222, exposing adhesive 1258 and absorbent member 1288. Slot, void or aperture 1247 is created by joining front base member 1217 and front top member 1219 together by inserting protrusion 1229 of front top member 1219 through aperture 1228 of front base member 1217. Aperture 1248 is formed in front base member 1217 and accepts needle 1210.

Figure 67:
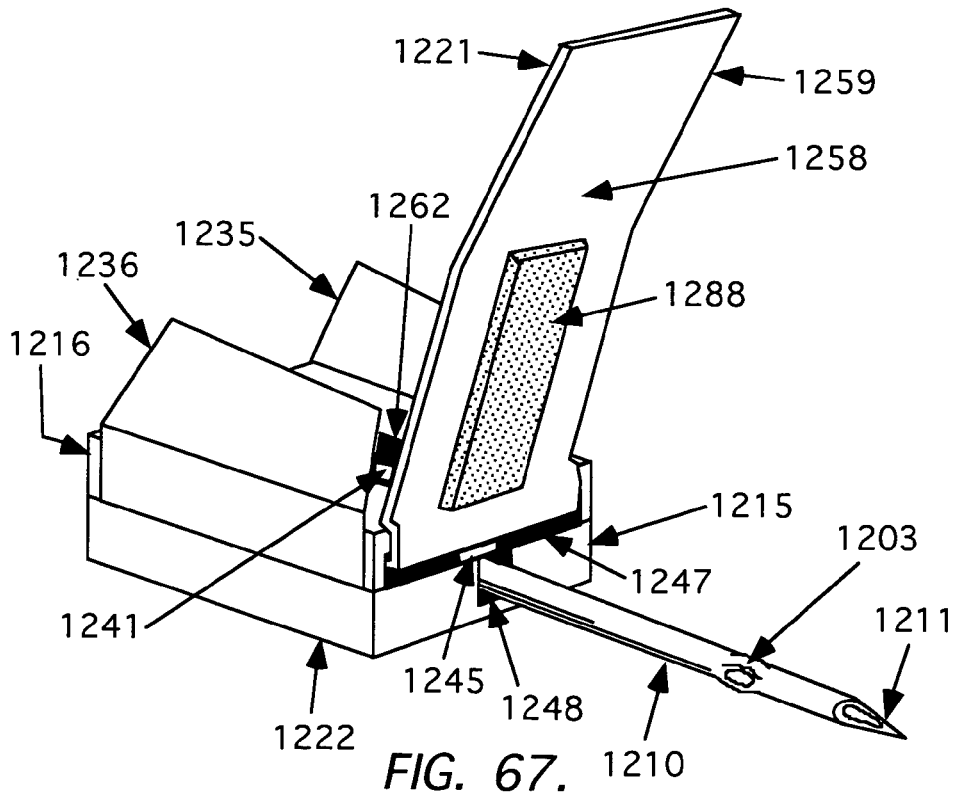
FIG. 67 is a full isometric view of a needle protective apparatus of the present invention showing an uncovered hypodermic needle having a needle guard with the bandage being further deployed from the needle guard and the release liner being fully separated from the adhesive face or faces of the bandage.

FIG. 67 is a full isometric view of a needle protective apparatus 1222 of the present invention joined together by mating top 1216 and bottom 1215 members showing a partially deployed puncture site cover or bandage 1259 now fully released from liner 1234. Liner 1236 and separate liner 1235 have released hold on bandage 1259 and are attached to said guard 1222 when mating top 1216 and bottom 1215 members are joined together. Hypodermic needle 1210 having a sharpened distal tip 1211 and enlargement 1203 to limiting axial movement of guard 1222 on said needle 1210. Bandage 1259 having an absorbent member 1288 for covering a puncture site and adhesive film or coating 1258 for securing about a puncture site. As extended end 1221 of bandage 1259 is moved away from guard 1222, releasable liner 1234 remains attached to said guard 1222, exposing adhesive 1258 and absorbent member 1288. Slot, void or aperture 1262 in top 1223 of needle guard 1222 is created by forming of movable needle trap 1241 hinged to rear member 1218.

Figure 68:
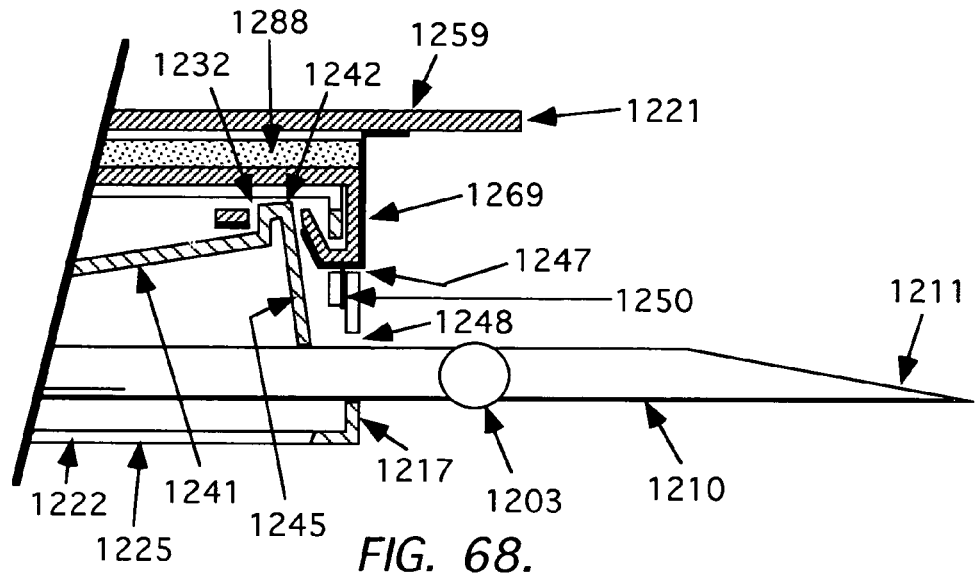
FIG. 68 is a full side view of an exposed, ready to use hypodermic needle and a partial cutaway view of a slidable needle guard having a movable needle trap shown in a first operable position with a releasable bandage shown in a first operable position and mechanically locked to said movable need trap where the adhesive face of said bandage has a releasable liner attached to said adhesive face of said bandage and a portion of said liner is also secured to said needle guard.

FIG. 68 is another full side view of FIG. 64 showing bandage 1259 releasable attached to top 1223 of movable needle guard 1222 with exposed, ready to use hypodermic needle 1210 having a change in profile or enlargement 1203 on the shaft proximal to the sharpened distal tip 1211 and, and a partial cutaway view of slidable needle guard 1222 having movable needle trap 1241 shown in a first operable position, said needle trap 1241 having a protrusion 1242 for retaining aperture 1232 of member or adhesive coated bandage 1259 in a first operative position, said bandage 1259 having an aperture 1232, and absorbent member 1288, extended tab 1221 for gripping, and an adhesive coating 1258. A liner 1269, separate from the above referenced liner 1234, 1235 and 1236, is secured at 1250 to said guard 1222 between front base member 1217 and front top member 1219 and covers distal portion of bandage 1258 maintaining sterility until said bandage 1259 is deployed. Said liner 1269 may also be joined or folded onto guard 1222. Needle guard 1222 formed having top 1223 with an axial slot 1262 formed by the manufacture of said needle guard 1241, bottom 1255, rear 1218 having aperture 1270 for accepting a hypodermic needle 1210 and hinge 1240 connecting movable needle trap 1241 to needle guard 1222, and a front base side 1217.

Figure 69:
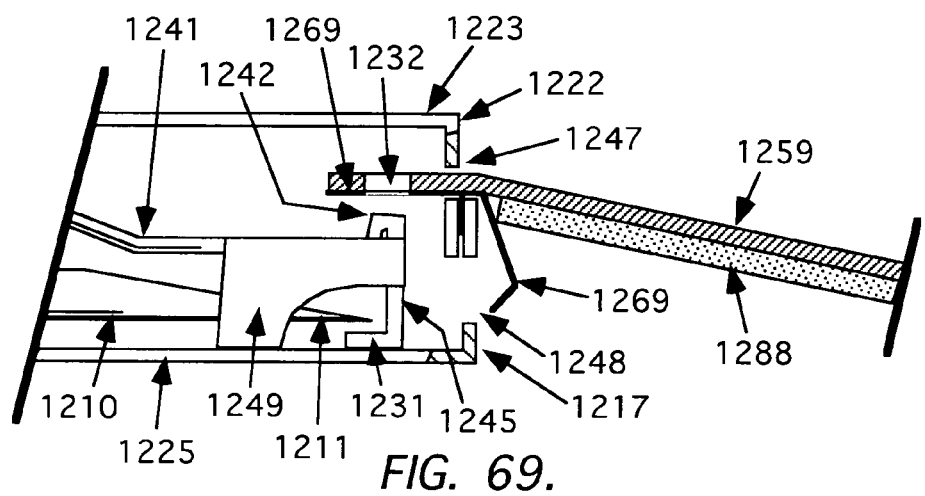
FIG. 69 is a full side view of a covered hypodermic needle and a partial cutaway view of the slidable needle guard of FIG. 68 showing the movable needle trap in a second position covering the needle tip with the movable needle trap having a plurality of skirts forming a containment chamber with the releasable bandage shown in a second covering position over a puncture site now fully separated from the lock of said need trap where a portion of the adhesive face of said bandage has separated from the releasable liner attached to said adhesive face of said bandage, and a portion of said liner is secured to said needle guard.

FIG. 69 is a full side view the needle protective apparatus of FIG. 68 showing bandage 1259 deployed over puncture site and released from lock of protrusion 1242 of movable needle guard 1222 with needle tip 1211 now contained within needle guard 1222 by movable needle guard 1241 having a distal barrier 1245 and side members 1249. Said guard 1222 with movable needle trap 1241 shown in a second position covering needle tip 1211. Bandage 1259 is further separated from liner 1269 secured to guard 1222.

Figure 70:
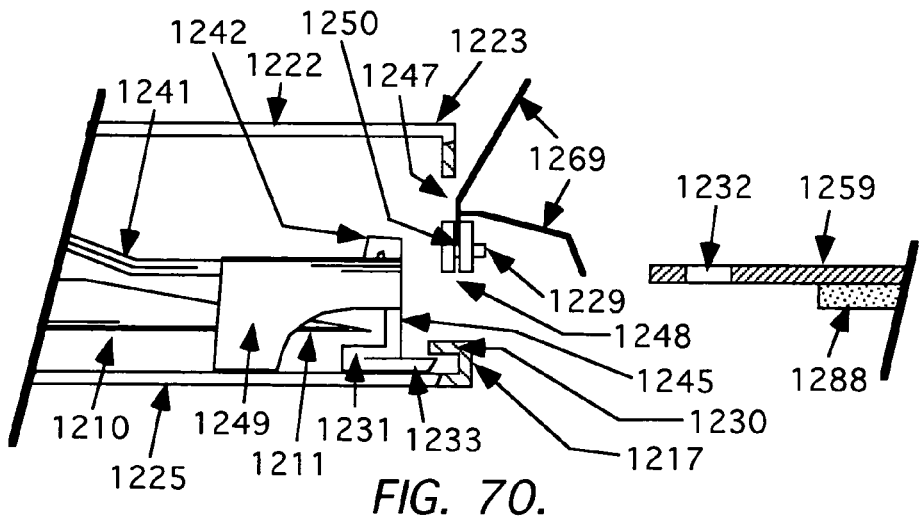
FIG. 70 is a full side view of a covered hypodermic needle and a partial cutaway view of the slidable needle guard of FIGS. 68 and 69 showing the movable needle trap in a second locked position covering the needle tip with the movable needle trap having a plurality of a skirts forming a containment chamber with the releasable bandage shown in a third covering position now fully separated from said needle guard where the entire adhesive face of said bandage has completely separated from the releasable liner that is secured to said needle guard.

FIG. 70 is a full side view and partial cutaway view of a the needle protective apparatus of the present invention showing slidable needle guard of FIGS. 68 and 69 having bandage 1259 deployed over puncture site and said bandage 1259 fully separated from needle guard 1222 with needle tip 1211 now contained within needle guard 1222 by movable needle guard 1241 shown in a second locked position by engagement of protrusion 1233 of needle trap 1241 and protruding member 1230 of front base 1217 of needle guard 1222, said guard 1241 having a distal barrier 1245 and side members 1249 creating a containment chamber. Bandage 1259 is completely separated from liner 1269 secured to guard 1222. By combining bandage 1259 with releasable liner of FIGS. 66 and 67 and releasable liner 1269, the user simply deploys bandage 1259 over puncture site and withdraws needle 1210, both needle and puncture site are covered automatically requiring no additional steps.

Figure 71:
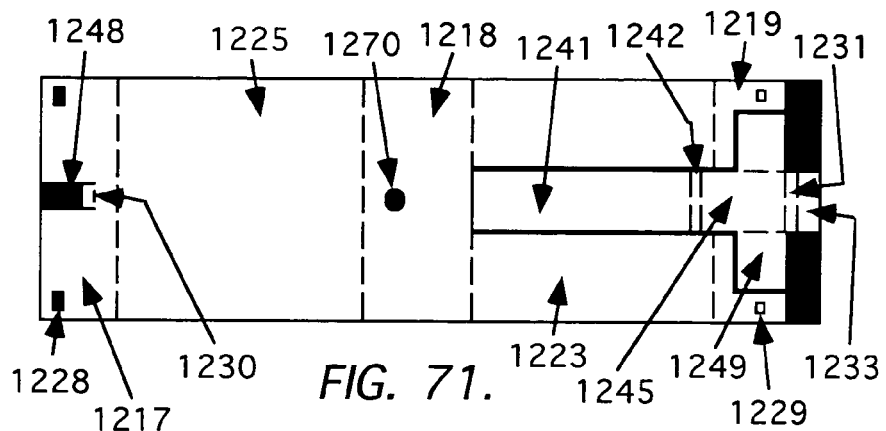
FIG. 71 is a full top view of a sheet, flat or plate of material having a series of cut outs, stampings and foldable portions for bending and forming into a needle guard with at least one movable needle trap having a lock for securing a releasable member or bandage to said needle guard, a means for locking the needle trap in a second position covering an aperture and containing a needle tip, and a means for joining portions of said needle guard together.

FIG. 71 is a full top view of a sheet, flat or plate of material having a series of cut outs, stampings 1228, 1229, 1230, 1231, 1233, 1241, 1242, 1245, 1248, 1249, 1270 and foldable portions for bending and forming sheet into needle guard 1222 with at least one movable needle trap 1241 having an extended member 1233 for engaging protrusion 1230 of front member 1217 to lock needle trap 1241 into a second protective position containing contaminated needle tip 1211. Said needle trap 1241 having a lock 1242 for securing a releasable member or bandage 1259 to said needle guard 1222, and a means for joining portions 1217 and 1219 of said needle guard 1222 together by joining protrusion 1229 into aperture 1228.

Figure 72:
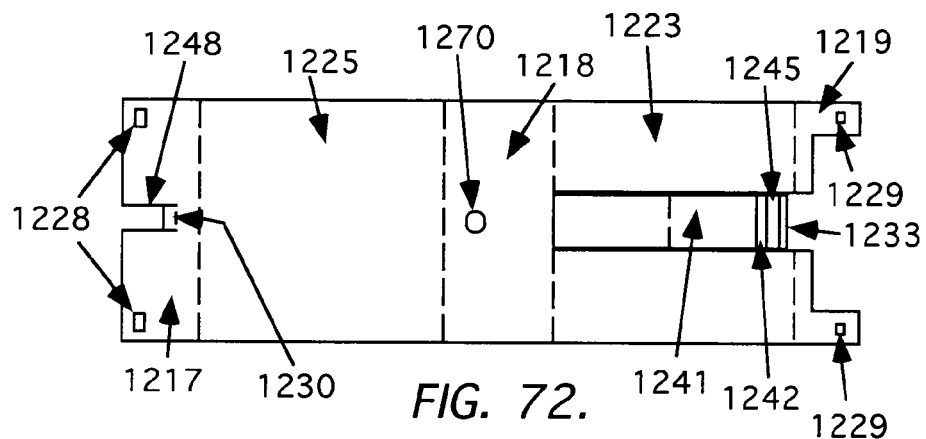
FIG. 72 is a full top view of the sheet, flat or plate of material of FIG. 71 showing a partially formed movable needle guard having a plurality of members forming a barrier, containment chamber and protrusion formed by folding and bending portions of said sheet.

FIG. 72 is a full top view of the sheet, flat or plate of material of FIG. 71 showing a partially formed movable needle guard 1241 having a plurality of members 1242 and 1245 forming a barrier, containment chamber and protrusions 1230, 1233, 1249 formed by folding and bending portions of said sheet or substrate.

Figure 73:
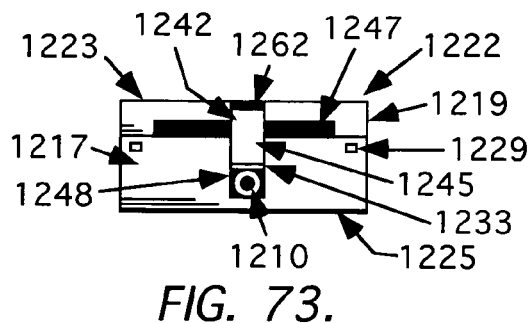
FIG. 73 is a full front view of a hypodermic needle and the needle guard of the present invention formed from a single sheet, flat or plate of material having a movable needle trap with a lock for securing a releasable member or bandage through an aperture, a means for locking the needle trap in a second position to contain a needle tip within the needle guard, and an aperture for a hypodermic needle and a means for joining portions of said sheet, flat or plate together.

FIG. 73 is a full front view of the needle protective apparatus of the present invention as shown in FIG. 66 without bandage 1259 showing hypodermic needle 1210 extending from needle guard 1222 having movable needle trap 1241 biased against needle 1210 with lock 1242 for securing releasable member or bandage 1259 through aperture 1247, an extending member or protrusion for 1233 locking needle trap 1241 in a second position to contain needle tip 1211 within needle guard 1222, and an aperture 1248 for a hypodermic needle 1210 and a means for joining portions of said sheet, flat or plate together by joining and bending protrusion 1229 through aperture 1228.

Figure 74:
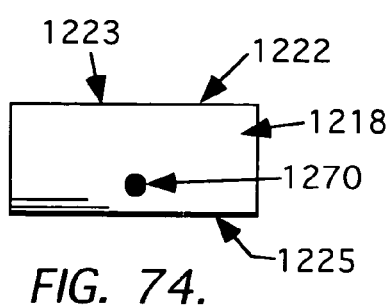
FIG. 74 is a full rear view of the needle guard of FIG. 73 having an aperture for a hypodermic needle, said aperture may also be a limiting means.

FIG. 74 is a full rear view of the needle guard of FIG. 73 having aperture 1270 for a hypodermic needle 1210, said aperture 1270 may also be a limiting means for limiting axial movement by engaging enlargement 1203 of needle 1210.

Figure 75:
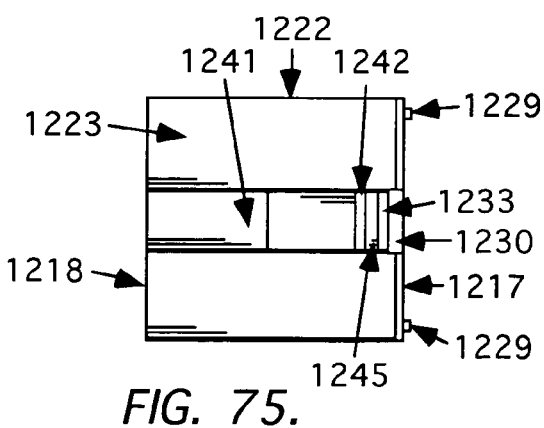
FIG. 75 is a full top view of the needle guard of FIGS. 73 and 74 having a hinged movable needle trap with a lock for securing a releasable member or bandage through an aperture, a plurality of protrusions for locking the needle trap in a second position to contain a needle tip within the needle guard, and a means for joining portions of said sheet, flat or plate together to create said needle guard.

FIG. 75 is a full top view of the needle guard 1222 of FIGS. 73 and 74 having a hinged movable needle trap 1241 with a traverse distal barrier 1245, said trap needle 1241 having lock or protrusion 1242 for securing releasable member or bandage 1259 through aperture 1247, a plurality of protrusions 1233 and 1230 for locking the needle trap in a second position to contain needle tip 1211 within needle guard 1222, and a means for joining portions of said sheet, flat or plate together to create said needle guard when front base member 1217 is joined together with adjoining front top member 1219.

Figure 76:
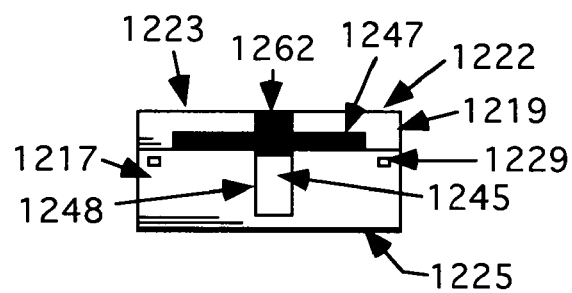
FIG. 76 is a full front view of the needle guard of FIG. 73 formed from a single sheet, flat or plate of material showing the movable needle trap locked in a second position covering the needle tip and closing the aperture.

FIG. 76 is a full front view of the needle guard 1222 of FIG. 73 showing distal barrier 1245 of movable needle trap 1241 closing aperture 1248 and locked in a second protective position covering needle tip 1211 now securely contained within said needle guard 1222.

Figure 77:
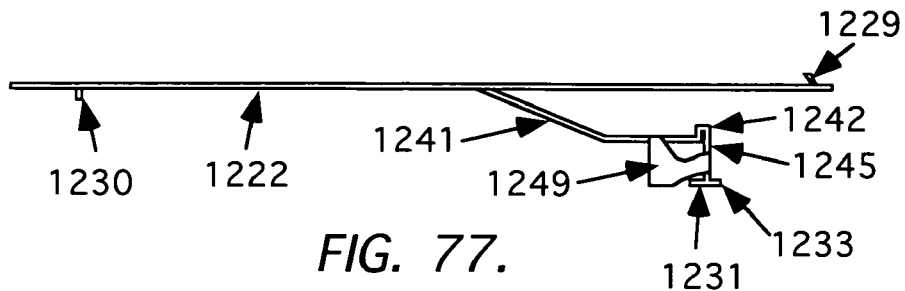
FIG. 77 is a full and partial cutaway side view of the needle guard of FIG. 72 in the first phase of forming.

FIG. 77 is a full and partial cutaway side view of needle guard 1222 of FIG. 72 in the first phase of forming where movable needle trap 1241 is hingedly attached to body 1222, said needle trap 1241 having side members 1249, a bottom or lower member 1231 and creating a chamber, and an extending member 1233 for engaging lock or protrusion 1230 of face member 1217. Movable needle trap 1241 is formed to move from an operative position to a protective position when used in combination with hypodermic needle 1210 and needle guard 1222 as described herein.

Figure 78:
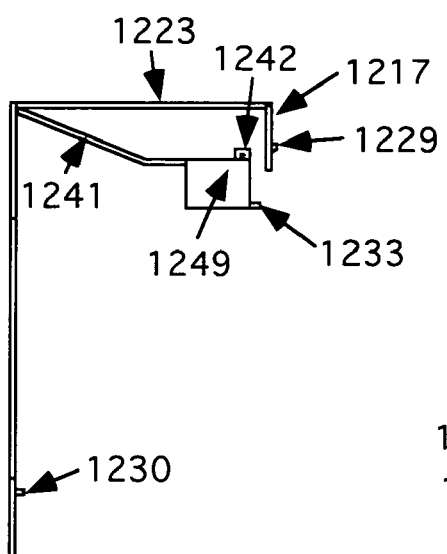
FIG. 78 is a full side view of the needle guard of FIG. 77 having a top, front and rear members created by bending or folding portions of said sheet, flat or plate to create said needle guard.

FIG. 78 is a full side view of the needle guard of FIG. 77 in a subsequent phase of forming having top 1223, bottom 1225, front 1217 and 1219 and rear 1218 members created by bending or folding portions of said sheet, flat or plate to create said needle guard 1222.

Figure 79:
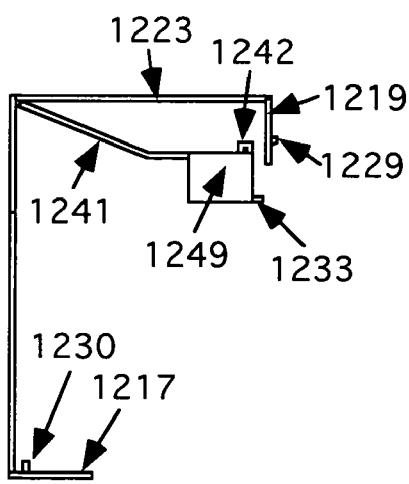
FIG. 79 is a full side view of the needle guard of FIG. 77 and 78 having a top, front, rear and joinable members created by bending or folding portions of said sheet, flat or plate to create said needle guard.

FIG. 79 is a full side view of the needle guard of FIG. 77 and 78 77 in a subsequent phase of forming having a top 1223, front 1217 and 1219, rear 1218 and joinable members created by bending or folding portions of said sheet, flat or plate to create said needle guard 1222.

Figure 80:
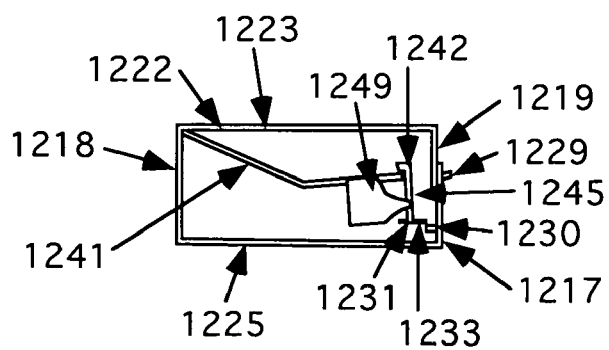
FIG. 80 is a full side view of the needle guard of FIG. 77, 78 and 79 having a top, bottom, rear and front created by and bending and joining portions of said sheet, flat or plate to create said needle guard that is ready to accept a hypodermic needle and releasable bandage.

FIG. 80 is a full side view of the needle guard of FIG. 77, 78 and 79 having a top 1223, bottom 1225, rear 1218 and front 1217 and 1219 created by and bending and joining portions of said sheet, flat or plate to create said needle guard 1222 that is ready to accept a hypodermic needle 1210 and releasable bandage 1259.

A number of embodiments have been disclosed herein as they relate to the puncture site indicator and needle protective device of the present invention. It is important to understand that many of the elements described herein may be interchangeable. It is also important to note that the invention can comprise a variety of embodiments, ranging from a single piece, injection molded part, where the components are manufactured unitarily, to a plurality of components, all which achieve the desired result of marking or covering the puncture site or safely capturing the sharpened needle tip.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A system for covering the puncture site made by a hypodermic needle having a longitudinal axis, a proximal end and a sharpened distal end comprising:

a sliding member having a distal end with a opening and one or more sides extending proximally from the distal end that are non-orthogonal to the longitudinal axis of the hypodermic needle, wherein the one or more sides has an inner surface and an outer surface, the sliding member axially mounted upon said needle and operative to move along the length thereof; and a protective covering mounted on only a portion of the outer surface of at least one of the sides of said sliding member and having a protrusion that extends at least partially distal to the distal end of the sliding member, the protective covering having an absorbent coupled to an adhesive for securing the covering about the puncture site, the protective covering being deployable from the at least one side by use of the protrusion to lie over and cover said puncture site formed by said distal end of said needle.

2. The system of claim 1 wherein said sliding member comprises a sleeve.

3. The system of claim 1 wherein said covering comprises a bandage.

4. The system of claim 1 wherein said covering is provided with a medication to be administered about said puncture site.

5. The system of claim 1 wherein said medication is selected from the group consisting of a topically applied antibiotic, anti-inflammatory agent and anesthetic agent.

6. The system of claim 1 wherein said system further includes a needle hub at a proximal end of the needle and a tether securing said sliding member to said hub.

7. The system of claim 1 wherein said sliding member is operative to cover the sharpened distal end of said needle, the sliding member configured to limit both proximal and distal movement of the sliding member along the needle once the sharpened distal end of said needle is covered.

8. The system of claim 7 wherein said system further comprises a change in profile formed along said needle for engaging with said sliding member, said change in profile limiting distal movement of said sliding member along said needle.

9. The system of claim 1 wherein the protective covering is deployable by sliding, unrolling or unfolding at least a portion of the protective covering from the at least one side of the sliding member.

10. The system of claim 1 wherein said protective covering comprises a bandage having an aperture that engages with at least a portion of the sliding member for releasably retaining said bandage to said sliding member.

11. A system for covering the puncture site made by a hypodermic needle having a proximal end and a sharpened distal end comprising:

a sliding member axially mounted upon said needle and operative to move along the length thereof, the sliding member including a moveable arm having a protrusion; and a bandage attached to the sliding member and operative to lie over and cover the puncture site formed by the distal end of the needle, the bandage having an aperture, the sliding member protrusion being engaged with the bandage aperture so as to interact with one another in a manner to cause, during normal use of the device, the bandage to be detachable from the sliding member only when the sliding member is positioned to cover the distal end of the needle.

* * * * *